United States Patent
Davis et al.

(10) Patent No.: US 8,241,359 B2
(45) Date of Patent: Aug. 14, 2012

(54) TRANSFORAMINAL INTERSOMATIC CAGE FOR AN INTERVERTEBRAL FUSION GRAFT AND AN INSTRUMENT FOR IMPLANTING THE CAGE

(75) Inventors: Reginald James Davis, Cockeysville, MD (US); Kevin Kaufman, Ft. Worth, TX (US); Greg Hoffman, Fort Wayne, IN (US); Alan McGee, Fort Wayne, IN (US); Jean Huppert, L'etrat (FR); Hugues Mousselard, Paris (FR); Ludovic Rillardon, Le Raincy (FR)

(73) Assignee: LDR Medical, Rosières Près Troyes (FR)

( * ) Notice: Subject to any disclaimer, the term of this patent is extended or adjusted under 35 U.S.C. 154(b) by 655 days.

(21) Appl. No.: 12/279,664

(22) PCT Filed: Feb. 15, 2007

(86) PCT No.: PCT/IB2007/000367
§ 371 (c)(1),
(2), (4) Date: Apr. 22, 2009

(87) PCT Pub. No.: WO2007/093900
PCT Pub. Date: Aug. 23, 2007

(65) Prior Publication Data
US 2009/0222092 A1     Sep. 3, 2009

(30) Foreign Application Priority Data

Feb. 15, 2006    (FR) ...................................... 06 01315

(51) Int. Cl.
*A61F 2/44*    (2006.01)
(52) U.S. Cl. ..................... 623/17.11; 623/17.16; 606/99

(58) Field of Classification Search ............... 623/17.11, 623/17.16; 606/99
See application file for complete search history.

(56) References Cited

U.S. PATENT DOCUMENTS
4,714,469 A    12/1987    Kenna
(Continued)

FOREIGN PATENT DOCUMENTS
DE            3741493 A1    6/1989
(Continued)

OTHER PUBLICATIONS

Transforanimal intersomatic cage for an intervertebral fusion graft and an instrument for implanting the cage, U.S. Appl. No. 11/378,165, Mar. 17, 2006.

(Continued)

*Primary Examiner* — Thomas J Sweet
*Assistant Examiner* — Megan Wolf
(74) *Attorney, Agent, or Firm* — Denko Coburn & Lauff LLP

(57) ABSTRACT

This present invention concerns a transforaminal intersomatic cage for an intervertebral fusion graft, and an instrument and method for implanting the cage, an embodiment of the cage having a body in the shape of a circular arc and comprising a lateral concave surface, a lateral convex surface, a straight upper surface, a straight lower surface and an end wall having at least one hole, called the end hole, designed to receive a rod of an instrument for implanting the cage between the vertebrae, wherein: the end hole has an orientation that is more or less tangential to the circular arc described by the body; the extremity opposite to the end wall of the body includes a return part extending the body toward the center of the circle on which the circular arc described by the body lies.

26 Claims, 6 Drawing Sheets

U.S. PATENT DOCUMENTS

| | | | |
|---|---|---|---|
| 4,904,261 A | 2/1990 | Dove et al. | |
| 4,997,432 A | 3/1991 | Keller | |
| 5,192,327 A | 3/1993 | Brantigan | |
| 5,246,458 A | 9/1993 | Graham | |
| 5,306,307 A | 4/1994 | Senter et al. | |
| 5,306,309 A | 4/1994 | Wagner et al. | |
| 5,397,364 A | 3/1995 | Kozak et al. | |
| 5,425,772 A | 6/1995 | Brantigan | |
| 5,458,638 A | 10/1995 | Kuslich et al. | |
| 5,534,029 A | 7/1996 | Shima | |
| 5,554,191 A | 9/1996 | Lahille et al. | |
| 5,571,109 A | 11/1996 | Bertagnoli | |
| 5,609,636 A | 3/1997 | Kohrs et al. | |
| 5,713,899 A | 2/1998 | Marnay et al. | |
| 5,741,253 A | 4/1998 | Michelson | |
| 5,755,798 A | 5/1998 | Papavero et al. | |
| 5,766,252 A | 6/1998 | Henry et al. | |
| 5,772,661 A | 6/1998 | Michelson | |
| 5,776,199 A | 7/1998 | Michelson | |
| 5,782,919 A | 7/1998 | Zdeblick et al. | |
| 5,797,909 A | 8/1998 | Michelson | |
| 5,800,550 A | 9/1998 | Sertich | |
| 5,860,973 A | 1/1999 | Michelson | |
| 5,865,845 A | 2/1999 | Thalgott | |
| 5,888,223 A | 3/1999 | Bray | |
| 5,888,224 A | 3/1999 | Beckers et al. | |
| 5,984,967 A | 11/1999 | Zdeblick et al. | |
| 6,001,130 A | 12/1999 | Bryan et al. | |
| 6,033,438 A | 3/2000 | Bianchi et al. | |
| 6,045,579 A | 4/2000 | Hochshuler et al. | |
| 6,059,787 A | 5/2000 | Allen | |
| 6,063,121 A | 5/2000 | Xavier et al. | |
| 6,080,158 A | 6/2000 | Lin | |
| 6,080,193 A | 6/2000 | Hochshuler et al. | |
| 6,093,205 A | 7/2000 | McLeod et al. | |
| 6,096,038 A | 8/2000 | Michelson | |
| 6,096,080 A | 8/2000 | Nicholson | |
| 6,111,164 A | 8/2000 | Rainey et al. | |
| 6,113,637 A | 9/2000 | Gill et al. | |
| 6,113,638 A | 9/2000 | Williams et al. | |
| 6,120,502 A | 9/2000 | Michelson | |
| 6,123,705 A | 9/2000 | Michelson | |
| 6,136,031 A | 10/2000 | Middleton | |
| 6,143,032 A * | 11/2000 | Schafer et al. | 623/17.11 |
| 6,146,421 A | 11/2000 | Gordon et al. | |
| 6,149,650 A | 11/2000 | Michelson | |
| 6,156,067 A | 12/2000 | Bryan et al. | |
| 6,174,311 B1 * | 1/2001 | Branch et al. | 606/86 A |
| 6,179,875 B1 | 1/2001 | Von Strempel | |
| 6,193,757 B1 | 2/2001 | Foley et al. | |
| 6,206,922 B1 | 3/2001 | Zdeblick et al. | |
| 6,206,923 B1 | 3/2001 | Boyd et al. | |
| 6,210,412 B1 | 4/2001 | Michelson | |
| 6,224,595 B1 | 5/2001 | Michelson | |
| 6,235,059 B1 | 5/2001 | Benezech et al. | |
| 6,241,769 B1 | 6/2001 | Nicholson et al. | |
| 6,241,770 B1 | 6/2001 | Michelson | |
| 6,245,072 B1 | 6/2001 | Zdeblick et al. | |
| 6,245,108 B1 | 6/2001 | Biscup | |
| 6,251,140 B1 | 6/2001 | Marino et al. | |
| 6,258,125 B1 | 7/2001 | Paul et al. | |
| 6,264,656 B1 | 7/2001 | Michelson | |
| 6,267,764 B1 | 7/2001 | Elberg | |
| 6,270,498 B1 | 8/2001 | Michelson | |
| 6,277,149 B1 | 8/2001 | Boyle et al. | |
| 6,296,664 B1 | 10/2001 | Middleton | |
| 6,302,914 B1 | 10/2001 | Michelson | |
| 6,306,170 B2 | 10/2001 | Ray | |
| 6,315,797 B1 | 11/2001 | Middleton | |
| 6,342,074 B1 | 1/2002 | Simpson | |
| 6,348,071 B1 | 2/2002 | Steffee et al. | |
| 6,350,283 B1 | 2/2002 | Michelson | |
| 6,364,880 B1 | 4/2002 | Michelson | |
| 6,371,988 B1 | 4/2002 | Pafford et al. | |
| 6,375,655 B1 | 4/2002 | Zdeblick et al. | |
| 6,395,031 B1 | 5/2002 | Foley et al. | |
| 6,395,035 B2 | 5/2002 | Bresina et al. | |
| 6,402,750 B1 | 6/2002 | Atkinson et al. | |
| 6,402,785 B1 | 6/2002 | Zdeblick et al. | |
| 6,409,765 B1 | 6/2002 | Bianchi et al. | |
| 6,419,704 B1 | 7/2002 | Ferree | |
| 6,423,095 B1 | 7/2002 | Van Hoeck et al. | |
| 6,432,106 B1 | 8/2002 | Fraser | |
| 6,432,107 B1 | 8/2002 | Ferree | |
| 6,447,512 B1 | 9/2002 | Landry et al. | |
| 6,447,544 B1 | 9/2002 | Michelson | |
| 6,447,546 B1 | 9/2002 | Bramlet et al. | |
| 6,447,547 B1 | 9/2002 | Michelson | |
| 6,454,769 B2 | 9/2002 | Wagner et al. | |
| 6,458,159 B1 | 10/2002 | Thalgott | |
| 6,461,359 B1 | 10/2002 | Tribus et al. | |
| 6,468,310 B1 | 10/2002 | Ralph et al. | |
| 6,471,724 B2 | 10/2002 | Zdeblick et al. | |
| 6,478,823 B1 | 11/2002 | Michelson | |
| 6,482,233 B1 | 11/2002 | Aebi et al. | |
| 6,500,205 B1 | 12/2002 | Michelson | |
| 6,524,312 B2 | 2/2003 | Landry et al. | |
| 6,527,806 B2 | 3/2003 | Ralph et al. | |
| 6,540,785 B1 | 4/2003 | Gill et al. | |
| 6,554,863 B2 | 4/2003 | Paul et al. | |
| 6,576,016 B1 | 6/2003 | Hochshuler et al. | |
| 6,579,291 B1 | 6/2003 | Keith et al. | |
| 6,582,468 B1 | 6/2003 | Gauchet | |
| 6,592,624 B1 | 7/2003 | Fraser et al. | |
| 6,599,320 B1 | 7/2003 | Kuslich et al. | |
| 6,605,089 B1 | 8/2003 | Michelson | |
| 6,610,065 B1 | 8/2003 | Branch et al. | |
| 6,610,089 B1 | 8/2003 | Liu et al. | |
| 6,610,092 B2 | 8/2003 | Ralph et al. | |
| 6,613,091 B1 | 9/2003 | Zdeblick et al. | |
| 6,616,671 B2 | 9/2003 | Landry et al. | |
| 6,635,087 B2 | 10/2003 | Angelucci et al. | |
| 6,645,206 B1 | 11/2003 | Zdeblick et al. | |
| 6,645,249 B2 | 11/2003 | Ralph et al. | |
| 6,652,584 B2 | 11/2003 | Michelson | |
| 6,660,038 B2 | 12/2003 | Boyer, II et al. | |
| 6,666,890 B2 | 12/2003 | Michelson | |
| 6,669,730 B2 | 12/2003 | Ralph et al. | |
| 6,669,731 B2 | 12/2003 | Ralph et al. | |
| 6,673,113 B2 | 1/2004 | Ralph et al. | |
| 6,676,703 B2 | 1/2004 | Biscup | |
| 6,679,887 B2 | 1/2004 | Nicholson et al. | |
| 6,679,915 B1 | 1/2004 | Cauthen | |
| 6,695,851 B2 | 2/2004 | Zdeblick et al. | |
| 6,695,882 B2 | 2/2004 | Bianchi et al. | |
| 6,706,067 B2 | 3/2004 | Shimp et al. | |
| 6,709,458 B2 | 3/2004 | Michelson | |
| 6,716,247 B2 | 4/2004 | Michelson | |
| 6,719,794 B2 | 4/2004 | Gerber et al. | |
| 6,733,504 B2 | 5/2004 | Lin et al. | |
| 6,733,531 B1 | 5/2004 | Trieu | |
| 6,733,535 B2 | 5/2004 | Michelson | |
| 6,736,850 B2 | 5/2004 | Davis | |
| 6,740,117 B2 | 5/2004 | Ralph et al. | |
| 6,740,118 B2 | 5/2004 | Eisermann et al. | |
| 6,743,255 B2 | 6/2004 | Ferree | |
| 6,743,256 B2 | 6/2004 | Mason | |
| 6,743,257 B2 | 6/2004 | Castro | |
| 6,749,636 B2 | 6/2004 | Michelson | |
| 6,758,849 B1 | 7/2004 | Michelson | |
| 6,767,367 B1 | 7/2004 | Michelson | |
| 6,770,074 B2 | 8/2004 | Michelson | |
| 6,793,679 B2 | 9/2004 | Michelson | |
| RE38,614 E | 10/2004 | Paul et al. | |
| 6,800,092 B1 | 10/2004 | Williams et al. | |
| 6,800,093 B2 | 10/2004 | Nicholson et al. | |
| 6,964,687 B1 | 11/2005 | Bernard et al. | |
| 6,994,727 B2 | 2/2006 | Khandkar et al. | |
| 7,018,412 B2 | 3/2006 | Ferreira et al. | |
| 7,037,340 B2 | 5/2006 | Gau | |
| 7,056,344 B2 | 6/2006 | Huppert et al. | |
| 7,060,097 B2 | 6/2006 | Fraser et al. | |
| 7,153,325 B2 | 12/2006 | Kim et al. | |
| 7,232,463 B2 | 6/2007 | Falahee | |
| 7,291,170 B2 | 11/2007 | Huppert | |
| 7,326,250 B2 | 2/2008 | Beaurain et al. | |
| 7,361,196 B2 | 4/2008 | Fallin et al. | |

| | | |
|---|---|---|
| 7,479,160 B2 | 1/2009 | Branch et al. |
| 7,494,508 B2 | 2/2009 | Zeegers |
| 7,507,248 B2 | 3/2009 | Beaurain et al. |
| 7,594,931 B2 | 9/2009 | Louis et al. |
| 7,604,654 B2 | 10/2009 | Fallin et al. |
| 7,625,393 B2 | 12/2009 | Fallin et al. |
| 7,632,282 B2 | 12/2009 | Dinville |
| 7,682,396 B2 | 3/2010 | Beaurain et al. |
| 7,695,516 B2 | 4/2010 | Zeegers |
| 7,695,518 B2 | 4/2010 | Gau |
| 7,842,088 B2 | 11/2010 | Rashbaum et al. |
| 8,002,835 B2 | 8/2011 | Zeegers |
| 2001/0020185 A1 | 9/2001 | Ray |
| 2002/0016592 A1 | 2/2002 | Branch et al. |
| 2002/0026243 A1 | 2/2002 | Lin |
| 2002/0082597 A1 | 6/2002 | Fraser |
| 2002/0107572 A1 | 8/2002 | Foley et al. |
| 2002/0151893 A1 | 10/2002 | Santilli |
| 2002/0165612 A1 | 11/2002 | Gerber et al. |
| 2002/0193880 A1 | 12/2002 | Fraser |
| 2003/0028249 A1 | 2/2003 | Baccelli et al. |
| 2003/0069640 A1* | 4/2003 | Ferreira et al. ............ 623/17.11 |
| 2003/0100950 A1 | 5/2003 | Moret |
| 2003/0109928 A1 | 6/2003 | Pasquet et al. |
| 2003/0149438 A1 | 8/2003 | Nichols et al. |
| 2003/0167091 A1 | 9/2003 | Scharf |
| 2003/0195514 A1 | 10/2003 | Trieu et al. |
| 2003/0195626 A1 | 10/2003 | Huppert |
| 2003/0195632 A1 | 10/2003 | Foley et al. |
| 2003/0204260 A1 | 10/2003 | Ferree |
| 2004/0073307 A1 | 4/2004 | Keller |
| 2004/0073309 A1 | 4/2004 | Bianchi et al. |
| 2004/0073313 A1 | 4/2004 | Link et al. |
| 2004/0093083 A1 | 5/2004 | Branch et al. |
| 2004/0117022 A1 | 6/2004 | Marnay et al. |
| 2004/0127990 A1 | 7/2004 | Bartish et al. |
| 2004/0127993 A1 | 7/2004 | Kast et al. |
| 2004/0127994 A1 | 7/2004 | Kast et al. |
| 2004/0148029 A1 | 7/2004 | Bianchi et al. |
| 2004/0162617 A1 | 8/2004 | Zucherman et al. |
| 2004/0172130 A1 | 9/2004 | Nakahara et al. |
| 2004/0199254 A1 | 10/2004 | Louis et al. |
| 2004/0243238 A1 | 12/2004 | Arnin et al. |
| 2004/0243240 A1 | 12/2004 | Beaurain et al. |
| 2005/0027359 A1 | 2/2005 | Mashburn |
| 2005/0027360 A1 | 2/2005 | Webb et al. |
| 2005/0038511 A1 | 2/2005 | Martz et al. |
| 2005/0060034 A1 | 3/2005 | Berry et al. |
| 2005/0085917 A1 | 4/2005 | Marnay et al. |
| 2005/0096745 A1* | 5/2005 | Andre et al. ............ 623/17.11 |
| 2005/0119747 A1 | 6/2005 | Fabris Monterumici et al. |
| 2005/0143733 A1 | 6/2005 | Petit |
| 2005/0149189 A1 | 7/2005 | Mokhtar et al. |
| 2005/0288788 A1 | 12/2005 | Dougherty-Shah |
| 2006/0069437 A1 | 3/2006 | Weber |
| 2006/0155377 A1 | 7/2006 | Beaurain et al. |
| 2006/0235426 A1* | 10/2006 | Lim et al. ........................ 606/99 |
| 2007/0073404 A1 | 3/2007 | Rashbaum et al. |
| 2007/0260249 A1 | 11/2007 | Boyajian et al. |
| 2007/0270951 A1 | 11/2007 | Davis et al. |
| 2008/0125865 A1 | 5/2008 | Abdelgany |
| 2008/0161933 A1 | 7/2008 | Grotz et al. |
| 2009/0105832 A1 | 4/2009 | Allain et al. |
| 2009/0204219 A1 | 8/2009 | Beaurain et al. |

FOREIGN PATENT DOCUMENTS

| | | |
|---|---|---|
| DE | 10323368 | 8/2004 |
| DE | 20320454 | 10/2004 |
| EP | 0965313 A | 12/1999 |
| FR | 2703580 A | 10/1994 |
| FR | 2733413 A1 | 10/1996 |
| FR | 2747034 A | 10/1997 |
| FR | 2808995 | 11/2001 |
| FR | 2823095 | 10/2002 |
| FR | 2827156 | 1/2003 |
| FR | 2846550 | 5/2004 |
| FR | 2861582 | 5/2005 |
| FR | 2891135 | 3/2007 |
| WO | WO9508306 | 3/1995 |
| WO | WO9715248 | 5/1997 |
| WO | WO9801091 A | 1/1998 |
| WO | WO9855052 A | 12/1998 |
| WO | WO9909914 A | 3/1999 |
| WO | WO9956676 A | 11/1999 |
| WO | WO0024327 | 5/2000 |
| WO | WO0170141 | 9/2001 |
| WO | WO0187194 | 11/2001 |
| WO | WO02/13732 | 2/2002 |
| WO | WO02089701 | 11/2002 |
| WO | WO03/005939 | 1/2003 |
| WO | WO03005939 | 1/2003 |
| WO | WO2004034935 | 4/2004 |
| WO | WO2004089256 | 10/2004 |
| WO | WO2007/078978 | 7/2007 |

OTHER PUBLICATIONS

Intersomatic cage with unified grafts, U.S. Appl. No. 11/767,386, Jun. 22, 2007.

Intersomatic cage, intervertebral prosthesis, anchoring device and implantation instruments, U.S. Appl. No. 12/134,884, filed Jun. 6, 2008.

Intervertebral Disc Prosthesis, U.S. Appl. No. 12/360,050, filed Jan. 26, 2009.

Vertebral Cage Device With Modular Fixation, U.S. Appl. No. 12/430,768, filed Apr. 27, 2009.

Progressive approach osteosynthesis device and preassembly method, U.S. Appl. No. 10/492,753, filed Aug. 9, 2004.

Plate for osteosynthesis device and preassembling method, U.S. Appl. No. 10/492,827, filed Jul. 15, 2004.

Implant for Osseous Anchoring with Polyaxial Head, U.S. Appl. No. 10/498,234, filed Dec. 7, 2004.

Osseous anchoring implant with a polyaxial head and method for installing the implant, U.S. Appl. No. 10/570,080, filed Jun. 9, 2006.

Device and method for sectioning a vertebral lamina, U.S. Appl. No. 10/575,065, filed Apr. 7, 2006.

Intervertebral Disc Prosthesis, U.S. Appl. No. 11/051,710, filed Feb. 4, 2005.

Intervertebral Disc Prosthesis and Instrumentation for Insertion of the Prosthesis Between the Vertebrae, U.S. Appl. No. 11/362,253, filed Feb. 24, 2006.

Intervertebral disc prosthesis insertion assemblies, U.S. Appl. No. 11/676,237, filed Feb. 16, 2007.

Modular intervertebral prosthesis, U.S. Appl. No. 11/874,144, filed Oct. 17, 2007.

Vertebral Support Device, U.S. Appl. No. 11/958,285, filed Dec. 17, 2007.

Intervertebral disc prosthesis, surgical methods, and fitting tools, U.S. Appl. No. 12/025,677, filed Feb. 4, 2008.

Transverse spinal linking device and system, U.S. Appl. No. 12/172,074, filed Jul. 11, 2008.

Spinal Osteosynthesis Device and Preparation Method, U.S. Appl. No. 12/409,327, filed Mar. 23, 2009.

Intervertebral Disk Prosthesis, U.S. Appl. No. 12/424,364, filed Apr. 15, 2009.

Instrumentation and Methods for Inserting an Intervertebral Disc Prosthesis, U.S. Appl. No. 12/435,955, filed May 5, 2009.

Intervertebral disc prosthesis insertion assemblies, U.S. Appl. No. 12/527,373, filed Aug. 14, 2009.

Implant for Osseous Anchoring with Polyaxial Head, U.S. Appl. No. 12/562,704, filed Sep. 18, 2009.

Intervertebral Disc Prosthesis, U.S. Appl. No. 12/955,898, filed Nov. 29, 2010.

Instruments and Methods for Removing Fixation Devices from Intervertebral Implants, U.S. Appl. No. 13/158,761, filed Jun. 13, 2011.

Intervertebral Disc Prosthesis, U.S. Appl. No. 13/215,123, filed Aug. 22, 2011.

Interspinous Implant and Implantation Instrument, U.S. Appl. No. 13/369,560, filed Feb. 9, 2012.

Cabinet Debay; Communication According to Rules 161 and 162 EPC in European Patent Application No. 07733892.9; European Patent Office; Berlin, German, All Pages.

WIPO; International Search Report in Application No. PCT/IB2007/000367; Oct. 22, 2007; WIPO; Geneva, Switzerland; All Pages.
WIPO; Written Opinion of the International Searching Authority in Application No. PCT/IB2007/000367; Oct. 22, 2007; WIPO; Geneva, Switzerland; All Pages.
WIPO; International Preliminary Report on Patentability in Application No. PCT/IB2007/000367; Feb. 5, 2008; WIPO; Geneva, Switzerland; All Pages.
Denko Coburn & Lauff LLP; Request for Continued Examination and Reply to Office Action in U.S. Appl. No. 11/378,165; Mar. 24, 2011; USPTO; Alexandria, Va.; All Pages.
USPTO; Office Action in U.S. Appl. No. 11/378,165 and Notice of References Cited; Sep. 24, 2010; USPTO; Alexandria, Va.; All Pages.
Civins Denko Coburn & Lauff LLP; Interview Summary in U.S. Appl. No. 11/378,165; Jun. 18, 2010; USPTO; Alexandria, Va.; All Pages.
USPTO; Interview Summary in U.S. Appl. No. 11/378,165 and Notice of References Cited; May 20, 2010; USPTO; Alexandria, Va.; All Pages.
Civins Denko Coburn & Lauff LLP; Reply to Office Action and Interview Request Form in U.S. Appl. No. 11/378,165; Apr. 26, 2010; USPTO; Alexandria, Va.; All Pages.
USPTO; Office Action in U.S. Appl. No. 11/378,165 and Notice of References Cited; Oct. 26, 2009; USPTO; Alexandria, Va.; All Pages.
USPTO; Advisory Action in U.S. Appl. No. 11/378,165; Aug. 11, 2009; USPTO; Alexandria, Va.; All Pages.
Civins Denko Coburn & Lauff LLP; Request for Continued Examination in U.S. Appl. No. 11/378,165; Aug. 14, 2009; USPTO; Alexandria, Va.; All Pages.
Civins Denko Coburn & Lauff LLP; Reply to Office Action in U.S. Appl. No. 11/378,165; Aug. 4, 2009; USPTO; Alexandria, Va.; All Pages.
USPTO; Office Action in U.S. Appl. No. 11/378,165 and Notice of References Cited; Feb. 17, 2009; USPTO; Alexandria, Va.; All Pages.
Fish & Richardson P.C.; Reply to Office Action in U.S. Appl. No. 11/378,165; Nov. 26, 2008; USPTO; Alexandria, Va.; All Pages.
USPTO; Office Action in U.S. Appl. No. 11/378,165 and Notice of References Cited; May 27, 2008; USPTO; Alexandria, Va.; All Pages.
Fish & Richardson P.C.; Reply to Restriction Requirement in U.S. Appl. No. 11/378,165; Feb. 28, 2008; USPTO; Alexandria, Va.; All Pages.
USPTO; Restriction Requirement in U.S. Appl. No. 11/378,165; Sep. 28, 2007; USPTO; Alexandria, Va.; All Pages.
FR 2 808 995 Preliminary Search Report, National Institute of Industrial Property (France), Jan. 29, 2001.
FR 2 827 156 Preliminary Search Report, National Institute of Industrial Property (France), Apr. 5, 2002.
Greffe et fusion, Website: http://www.ldrmedical.fr/roi.htm, Sep. 19, 2004.
Mc+ Le choix de l'ancrage, Website: http://www.ldrmedical.fr/mcplus.htm, Sep. 19, 2004.
PCT/FR01/01545, International Preliminary Examination Report, EPO, Aug. 30, 2002.
PCT/FR01/01545, International Search Report, EPO, Sep. 5, 2001.
PCT/IB02/03390, International Preliminary Examination Report, EPO, Nov. 6, 2003.
PCT/IB02/03390, International Search Report, EPO, Mar. 3, 2003.
ROI Privilegier la greffe en creant la chambre de fusion, Website: http://www.ldrmedical.fr/roi.htm, Sep. 19, 2004.
USPTO; Office Action in U.S. Appl. No. 12/134,884 and Notice of References Cited; Jan. 31, 2012; USPTO; Alexandria, Va.; All Pages.
WIPO; International Search Report in Application No. PCT/IB2008/001484; Feb. 16, 2009; WIPO; Geneva, Switzerland; All Pages.
WIPO; Written Opinion of the International Searching Authority in Application No. PCT/IB2008/001484; Feb. 16, 2009; WIPO; Geneva, Switzerland; All Pages.
WIPO; International Preliminary Report on Patentability in Application No. PCT/IB2008/001484; Aug. 5, 2009; WIPO; Geneva, Switzerland; All Pages.
Cabinet Debay; Article 34 Amendments in Application No. PCT/IB2008/001484; May 13, 2009; WIPO; Geneva, Switzerland; All Pages.

Cabinet Debay; Amendments in Application No. 08762820.2; Jan. 5, 2010; European Patent Office; Munich, Germany; All Pages.
European Patent Office; Office Action in Application No. 08762820.2; Jan. 17, 2012; European Patent Office; Munich, Germany; All Pages.
Institut National De La Propriete Industrielle; Preliminary Search Report in French Patent Application No. 0413728; Aug. 11, 2005; Institut National De La Propriete Industrielle; One Page.
Cabinet Debay; Amendments and Reply in European Patent Application No. 11165170; Mar. 6, 2012; European Patent Office; Munich, Germany; All Pages.
European Patent Office; Search report in Application No. 11165170; Jul. 21, 2011; European Patent Office; Munich, Germany; All Pages.
WIPO; Chapter II amendments in Application No. PCT/IB2005/004093; Nov. 16, 2006; WIPO; Geneva, Switzerland; All Pages.
WIPO; International Preliminary Report on Patentability in Application No. PCT/IB2005/004093; Feb. 22, 2007; WIPO; Geneva, Switzerland; All Pages.
WIPO; International Search Report in Application No. PCT/IB2005/004093; Aug. 31, 2006; WIPO; Geneva, Switzerland; All Pages.
WIPO; Written Opinion of the International Searching Authority in Application No. PCT/IB2005/004093; Aug. 31, 2006; WIPO; Geneva, Switzerland; All Pages.
USPTO; Notice of Allowance in U.S. Appl. No. 10/276,712; Jul. 30, 2007; USPTO; Alexandria, Va.; All Pages.
Fish & Richardson P.C.; Reply to Office Action in U.S. Appl. No. 10/276,712; Jun. 19, 2007; USPTO; Alexandria, Va.; All Pages.
USPTO; Office Action in U.S. Appl. No. 10/276,712 and Notice of References Cited; Dec. 20, 2006; USPTO; Alexandria, Va.; All Pages.
Fish & Richardson P.C.; Reply to Office Action in U.S. Appl. No. 10/276,712; Oct. 6, 2006; USPTO; Alexandria, Va.; All Pages.
USPTO; Office Action in U.S. Appl. No. 10/276,712; Jun. 7, 2006; USPTO; Alexandria, Va.; All Pages.
Andrews Kurth LLP; Reply to Office Action and RCE in U.S. Appl. No. 10/276,712; Jan. 17, 2006; USPTO; Alexandria, Va.; All Pages.
USPTO; Advisory Action in U.S. Appl. No. 10/276,712; Feb. 8, 2006; USPTO; Alexandria, Va.; All Pages.
USPTO; Office Action in U.S. Appl. No. 10/276,712; Nov. 14, 2005; USPTO; Alexandria, Va.; All Pages.
Andrews Kurth LLP; Reply to Office Action in U.S. Appl. No. 10/276,712; Aug. 29, 2005; USPTO; Alexandria, Va.; All Pages.
USPTO; Office Action and Notice of Reference Cited in U.S. Appl. No. 10/276,712; May 27, 2005; USPTO; Alexandria, Va.; All Pages.
Andrews Kurth LLP; Reply to Office Action and RCE in U.S. Appl. No. 10/276,712; Mar. 1, 2005; USPTO; Alexandria, Va.; All Pages.
USPTO; Office Action in U.S. Appl. No. 10/276,712; Dec. 23, 2004; USPTO; Alexandria, Va.; All Pages.
Lowe Hauptman Gilman and Berner LLP, Reply to Office Action in U.S. Appl. No. 10/276,712; Sep. 27, 2004; USPTO; Alexandria, Va.; All Pages.
USPTO; Office Action and Notice of References Cited in U.S. Appl. No. 10/276,712; Jun. 30, 2004; USPTO; Alexandria, Va.; All Pages.
Denko Coburn & Lauff LLP; Request for Continued Examination and Reply to Office Action in U.S. Appl. No. 11/767,386; Sep. 26, 2011; USPTO; Alexandria, Va.; All Pages.
USPTO; Office Action in U.S. Appl. No. 11/767,386; Mar. 24, 2011; USPTO; Alexandria, Va.; All Pages.
Denko Coburn & Lauff LLP; Reply to Office Action in U.S. Appl. No. 11/767,386; Jan. 21, 2011; USPTO; Alexandria, Va.; All Pages.
USPTO; Office Action and Notice of References Cited in U.S. Appl. No. 11/767,386; Jul. 21, 2010; USPTO; Alexandria, Va.; All Pages.
Civins Denko Coburn & Lauff LLP; Reply to Office Action in U.S. Appl. No. 11/767,386; Apr. 26, 2010; USPTO; Alexandria, Va.; All Pages.
USPTO; Office Action in U.S. Appl. No. 11/767,386; Dec. 24, 2009; USPTO; Alexandria, Va.; All Pages.
USPTO; Notice of Allowance in U.S. Appl. No. 10/483,563; Jun. 19, 2009; USPTO; Alexandria, Va.; All Pages.
Fish & Richardson P.C.; Reply to Office Action in U.S. Appl. No. 10/483,563; Apr. 28, 2009; USPTO; Alexandria, Va.; All Pages.
USPTO; Office Action and Notice of Reference Cited in U.S. Appl. No. 10/483,563; Oct. 28, 2008; USPTO; Alexandria, Va.; All Pages.

Fish & Richardson P.C.; Reply to Office Action in U.S. Appl. No. 10/483,563; Jul. 31, 2008; USPTO; Alexandria, Va.; All Pages.
USPTO; Office Action and Notice of Reference Cited in U.S. Appl. No. 10/483,563; Jan. 31, 2008; USPTO; Alexandria, Va.; All Pages.
Fish & Richardson P.C.; Reply to Office Action in U.S. Appl. No. 10/483,563; Nov. 19, 2007; USPTO; Alexandria, Va.; All Pages.
USPTO; Office Action and Notice of Reference Cited in U.S. Appl. No. 10/483,563; Oct. 30, 2007; USPTO; Alexandria, Va.; All Pages.
Fish & Richardson P.C.; Reply to Office Action in U.S. Appl. No. 10/483,563; Aug. 21, 2007; USPTO; Alexandria, Va.; All Pages.
USPTO; Office Action and Notice of Reference Cited in U.S. Appl. No. 10/483,563; Feb. 21, 2007; USPTO; Alexandria, Va.; All Pages.
USPTO; Corrected Notice of Allowability in U.S. Appl. No. 12/430,768; Jan. 19, 2012; USPTO; Alexandria, Va.; All Pages.
Denko Coburn & Lauff LLP; Reply to Office Action in U.S. Appl. No. 11/767,386; Dec. 14, 2011; USPTO; Alexandria, Va.; All Pages.
Denko Coburn & Lauff LLP; Terminal Disclaimer in U.S. Appl. No. 11/767,386; Dec. 13, 2011; USPTO; Alexandria, Va.; All Pages.
USPTO; Office Action and Notice of Reference Cited in U.S. Appl. No. 11/767,386; Jun. 14, 2011; USPTO; Alexandria, Va.; All Pages.
USPTO; Notice of Allowability, Examiner's Amendment, and Interview Summary in U.S. Appl. No. 11/109,276; Dec. 8, 2009; USPTO; Alexandria, Va.; All Pages.
Fish & Richardson P.C.; Reply to Office Action in U.S. Appl. No. 11/109,276; Aug. 4, 2009; USPTO; Alexandria, Va.; All Pages.
USPTO; Office Action in U.S. Appl. No. 11/109,276; Feb. 13, 2009; USPTO; Alexandria, Va.; All Pages.
Fish & Richardson P.C.; Reply to Office Action in U.S. Appl. No. 11/109,276; Jan. 26, 2009; USPTO; Alexandria, Va.; All Pages.
USPTO; Office Action in U.S. Appl. No. 11/109,276; Jul. 24, 2008; USPTO; Alexandria, Va.; All Pages.
Fish & Richardson P.C.; Reply to Office Action in U.S. Appl. No. 11/109,276; Apr. 16, 2008; USPTO; Alexandria, Va.; All Pages.
USPTO; Office Action in U.S. Appl. No. 11/109,276; Oct. 16, 2007; USPTO; Alexandria, Va.; All Pages.
Fish & Richardson P.C.; Reply to Office Action in U.S. Appl. No. 11/109,276; Aug. 6, 2007; USPTO; Alexandria, Va.; All Pages.
USPTO; Office Action and Notice of Reference Cited in U.S. Appl. No. 11/109,276; Feb. 6, 2007; USPTO; Alexandria, Va.; All Pages.
USPTO; Notice of Allowability in U.S. Appl. No. 12/360,050; Mar. 26, 2012; USPTO; Alexandria, Va.; All Pages.
Denko Coburn & Lauff LLP; Reply to Office Action in U.S. Appl. No. 12/360,050; Mar. 6, 2012; USPTO; Alexandria, Va.; All Pages.
USPTO; Office Action and Notice of Reference Cited in U.S. Appl. No. 12/360,050; Sep. 6, 2011; USPTO; Alexandria, Va.; All Pages.
Denko Coburn & Lauff LLP; Reply to Office Action in U.S. Appl. No. 12/360,050; Jun. 16, 2011; USPTO; Alexandria, Va.; All Pages.
USPTO; Office Action and Notice of Reference Cited in U.S. Appl. No. 12/360,050; Dec. 17, 2010; USPTO; Alexandria, Va.; All Pages.

* cited by examiner

TRANSFORAMINAL INTERSOMATIC CAGE FOR AN INTERVERTEBRAL FUSION GRAFT AND AN INSTRUMENT FOR IMPLANTING THE CAGE

CROSS REFERENCE TO RELATED APPLICATIONS

This application claims priority to French Patent Application No. FR0601315, filed in FRANCE on Feb. 15, 2006, which in incorporated herein by reference for all purposes.

BACKGROUND

This present invention concerns the area of intervertebral arthrodeses (fusion of two vertebrae) and in particular of intersomatic cages implanted between two adjacent vertebrae to allow the insertion and the growth of grafts of osseous tissue (or of substitute) in the disc space. In fact, after the insertion of the cage or implant, the intervertebral space is filled with autologous spongy bone or suitable bone substitutes. The invention also concerns an instrument for implanting the cage between the vertebrae, in particular through the transforaminal approach. The intersomatic cages are designed to be positioned between two vertebrae, in order to restore and/or maintain the disc space by replacing the intervertebral disc, and the grafts of osseous tissue or of substitute are designed to allow fusion between the two adjacent vertebrae between which they are inserted.

Various types of intersomatic cage are known from prior art. Some intersomatic cages known from prior art are machined from bone, most often cortical bone, so as to fuse with the graft inserted into the disc space. These cages composed of bone have the disadvantage to being capable of causing illness in the event of imperfect sterilisation.

Different intersomatic cages in solid materials of various types are also known from prior art. These cages include openings on their lower surface, their upper surface and on at least one of their lateral surfaces. One of these cages, in particular known from patent application WO0187194 (A1) submitted by the present applicant, has the shape of an open ring and can be used in combination with another cage of the same type by placing the open lateral surfaces of the two cages opposite to each other. Whatever the type of cage in question, spongy bone is compacted inside the cage, in order to finally achieve an osseous fusion (or arthrodesis) of the two vertebrae separated by a suitable disc space. Other cages known from previous designs are of parallelepiped shape, with the top and the bottom of the cage being completely open, and the top and bottom openings being designed to be positioned facing two vertebrae which have to be kept apart from each other. Openings created in the lateral faces of the parallelepipeds allow the graft to grow toward the exterior of the cage and possibly to reach a graft implanted in another cage also inserted into the disc space. These intersomatic cages have the disadvantage, firstly, of requiring a relatively large incision in the annulus (the outer part of the intervertebral disc), secondly, of requiring a relatively long time before achieving an arthrodesis, because of the confinement of the graft within a chamber at the centre of the cage and, thirdly, of having dimensions that are too large to be implanted through the transforaminal approach without partial or total ablation of the articular processes located posterior to the foramen through which the transforaminal approach runs.

Also known from previous designs in prior art, in particular from American patent application US 2005/0038511(A1), are intersomatic cages of various shapes and dimensions, machined from bone, and in particular an intersomatic cage of banana (or simple bracket) shape defining a longitudinal axis of the cage and having a lower surface and an upper surface, both straight, equipped with serrations and more or less parallel to the longitudinal axis of the cage, a concave lateral wall, a convex lateral wall, and two straight end walls that are more or less perpendicular to the top and bottom surfaces. One of the end walls of the cage includes a hole oriented toward the centre of the cage and intended to receive a rod of an instrument for insertion of the cage between the vertebrae. This intersomatic cage has the disadvantage of being in osseous tissue and therefore, as mentioned previously, of being capable of causing illness in the event of imperfect sterilisation. This cage may also have the disadvantage of eventually not being sufficiently solid to reliably take the stresses which will be applied to it when implanted in the disc space. Furthermore, this cage has the disadvantage of having a hole oriented toward the centre of the cage and in particular toward the centre of the concave surface, the result of which is to make the cage even more fragile. Moreover, the axis defined by this hole forms an angle, in relation to an axis parallel to a tangent to one of the concave and convex surfaces, that is too large to allow to an instrument for insertion of the cage between the vertebrae to fit onto the cage in an orientation that is more or less parallel to a tangent to one of the concave and convex surfaces. Thus, the orientation of the hole does not conform to the general curvature of the cage obtained by its convex and concave surfaces and does not allow an effective thrust to be applied to the cage on its axis of curvature. The cage, which is made fragile by this hole, is therefore in danger of breaking when pressure has to be applied at an angle that is too large in relation to the axis of curvature of the cage, which therefore proves difficult to implant by the transforaminal approach. Finally, withdrawal of the instrument inserted into the hole proves to be difficult due to the unsuitable orientation of the latter.

In this context, it is of interest to propose an intersomatic cage, preferably in a solid and sterile material, that has a shape and dimensions that make it suitable to be implanted through the transforaminal approach without an excessively large lesion of the articular processes, and having resources to fit onto an instrument for insertion of the cage between the vertebrae, with an orientation that conforms to the general shape of the cage. It is also of interest to propose an instrument for implanting the cage, and which is designed for the shapes and dimensions of the cage, allowing easy implantation of the cage between the vertebrae. Also known from prior art are previous designs of instruments for the implantation of intersomatic cages that have at least one rod designed to be inserted into a hole in the cage in order to hold the latter during passage through the foramen. However some of these instruments known from prior art require an ablation of at least one part of the articular processes impeding access to the foramen when the cage and the instrument have excessively large dimensions. Moreover, the transforaminal approach is relatively obstructed and is not perfectly straight. It is therefore desirable that the instrument should have an elbow (a curved or angled portion) at the end holding the cage. Some instruments known from prior art have dimensions that are small enough not to necessitate ablation of the articular processes, and some of these instruments have an angled portion that allows one to bypass the structure obstructing access to the disc space, but the rod designed to hold the cage, as well as the hole of the cage in which this rod is designed to be inserted, have an orientation that it not very compatible with the optimal thrust axis allowing insertion of the cage between the vertebrae and not very compatible with easy withdrawal of the rod when the cage has been implanted. It is therefore desirable to propose an instrument whose shape and dimensions are suitable for insertion using the transforaminal approach, having an angled portion to bypass the structures obstructing access to the disc space and having a rod designed to be inserted into a hole in the cage with an orientation that is optimal in order to facilitate the implantation of the cage between the vertebrae, and then withdrawal of the instrument.

SUMMARY

This present invention has as its objective to circumvent some disadvantages of the previous designs by proposing an intersomatic cage for an intervertebral fusion graft of suitable shape and of limited dimensions to be implanted through the transforaminal approach while also having adequate robustness to effectively maintain a disc space that allows the growth of the graft.

This objective is met by an intersomatic cage for an intervertebral fusion graft comprising a body generally defining an arc, the body comprising:
 a lateral concave surface;
 a lateral convex surface;
 a substantially transverse upper surface;
 a substantially transverse lower surface; an end wall at a first longitudinal extremity of the body, the end wall comprising an end hole configured to receive a retaining end of a rod of an implantation instrument and oriented substantially tangential to the arc defined by the body; and
 an incurvate return part at a second longitudinal extremity of the body opposite the end wall.

According to another feature, the end wall comprises a recess configured to receive a pin of an implantation instrument.

According to another feature, the return part comprises a return hole oriented substantially tangential to the arc defined by the body and configured to receive an end portion of an implantation instrument.

According to another feature, the end wall comprises a recess configured to receive a pin of an implantation instrument, the end hole, the recess, and the return hole being configured to cooperate with, respectively, a retaining end of a rod, a pin, and an end portion of an implantation instrument, to secure a grip on the intersomatic cage by the implantation instrument.

According to another feature, at least one of the upper and lower surfaces of the body comprises serrations oriented to oppose the movement of the intersomatic cage following intervertebral implantation of the intersomatic cage.

According to another feature, the return part comprises upper and lower surfaces extending, respectively, the upper and lower surfaces of the body, at least one of the upper and lower surfaces of the return part comprising serrations configured to oppose the movement of the intersomatic cage following intervertebral implantation of the intersomatic cage.

According to another feature, the return part comprises upper and lower surfaces extending, respectively, the upper and lower surfaces of the body, at least one of the upper and lower surfaces of the return part comprising a chamfer configured to facilitate the intervertebral implantation of the intersomatic cage.

According to another feature, the first and second longitudinal extremities of the body define a longitudinal axis of the intersomatic cage, and at least some of the serrations are oriented substantially parallel to the longitudinal axis of the intersomatic cage.

According to another feature, the first and second longitudinal extremities of the body define a longitudinal axis of the intersomatic cage, and at least some of the serrations are oriented substantially perpendicular to the longitudinal axis of the intersomatic cage.

According to another feature, the first and second longitudinal extremities of the body define a longitudinal axis of the intersomatic cage, and at least some of the serrations are disposed in a chevron configuration about an axis substantially perpendicular to the longitudinal axis of the intersomatic cage.

According to another feature, the first and second longitudinal extremities of the body define a longitudinal axis of the intersomatic cage, and at least some of the serrations define concentric circular arcs each being disposed symmetrically to the arc defined by the body, in relation to an axis of symmetry substantially parallel to the longitudinal axis of the intersomatic cage.

According to another feature, at least some of the serrations are oriented substantially normal to the arc defined by the body.

According to another feature, all of the serrations on the upper or lower surface of the intersomatic cage have substantially the same orientation.

According to another feature, some of the serrations on the upper or lower surface of the intersomatic cage do not have the same orientation as other serration on the same surface of the intersomatic cage.

According to another feature, serrations on each of the upper and lower surfaces of the intersomatic cage have the same orientation.

According to another feature, the serrations on the upper surface of the intersomatic cage have an orientation different from the orientation of the serrations on the lower surface of the intersomatic cage.

According to another feature, the body comprises a radio-opaque marker configured to identify the intersomatic cage in x-ray images.

According to another feature, the mean planes defined by the upper and lower surfaces of the cage are substantially parallel to each other.

According to another feature, the mean planes defined by the upper and lower surfaces of the cage form an angle allowing to correct defects of the spine.

According to another feature, at least one of the surfaces of the cage comprises at least one opening allowing the growth of a bony graft or substitute.

According to another feature, at least one slit passes through the body of the cage and forms a conduit extending form at least one of the surfaces of the cage to another, said slit being configured for receiving an anchor comprising a flat anchor plate intended to be impacted into a vertebral body with which the cage is in contact.

Another objective of this present invention is to propose an instrument for implanting an intersomatic cage between the vertebrae, facilitating access to the disc space and allowing a good grip to be obtained on the cage.

This objective is met by an instrument for the implantation of an intersomatic cage for an intervertebral fusion graft comprising a body generally defining an arc, the body comprising a lateral concave surface; a lateral convex surface; a substantially transverse upper surface; a substantially transverse lower surface; an end wall at a first longitudinal extremity of the body, the end wall comprising an end hole oriented substantially tangential to the arc defined by the body; said instrument comprising:
- a rod comprising a retaining end configured for insertion in the end hole;
- a gripping end for gripping the intersomatic cage, the gripping end comprising
  - a support spatula comprising a base and generally defining an arc complementary to the arc defined by the body,
  - a guide tube in which the rod is slidably disposed and to which the base of the support spatula is mounted, the guide tube comprising an opening through which the retaining end of the rod can transit for insertion in the end hole; and
- a handling end for manipulating the instrument.

According to another feature, the rod extends substantially to the vicinity of the handling end of the instrument.

According to another feature, the instrument comprises a button attached to the rod and a groove through which the button projects, the button being configured for sliding the rod to adjust the position of the retaining end of the rod in relation to the opening in the guide tube.

According to another feature, the guide tube comprises a pin configured to engage a recess disposed on the end wall of the intersomatic cage.

According to another feature, the support spatula comprises an end portion distal from the base, the end portion configured for insertion into a return hole disposed on an incurvate return part of the intersomatic cage, which return hole is oriented substantially tangential to the arc defined by the body.

According to another feature, the guide tube comprises a pin configured to engage a recess disposed on the end wall of the intersomatic cage, the retaining end of the rod, the pin, and the end portion of the implantation instrument being configured to cooperate with, respectively, the end hole, the recess, and the return hole, to secure a grip on the intersomatic cage by the implantation instrument, and to facilitate the withdrawal of the instrument following implantation of the intersomatic cage by removing the retaining end of the rod from the end hole.

According to another feature, the instrument further comprises an aiming tube that extends substantially to the vicinity of the handling end of the instrument, wherein the guide tube comprises a mobile portion that pivots in relation to the aiming tube at least in a primary pivot direction, the primary pivot direction lying substantially within a plane in which the arc defined by the support spatula lies, and the position of the mobile portion in relation to the aiming tube defining a pivot angle.

According to another feature, one of the mobile portion or the aiming tube comprises a substantially spherical end, and the other of the mobile portion or the aiming tube comprises a recessed end having a shape and dimensions complementary to the shape and dimensions of the spherical end, the spherical end and the recessed end being configured, respectively, as a ball component and a socket component of a ball and socket connection.

According to another feature, the socket component comprises opening edge portions, one of which portions is proximal to the support spatula and is configured to encompass the ball component less than the other opening edge portions to allow further pivoting of the mobile portion in relation to the aiming tube at least in the primary pivot direction.

According to another feature, the rod is flexible and slidably transits the ball and socket connection through a channel located at the centre of the ball component and the socket component, the channel having a hollowed portion proximal to the support spatula, the hollowed portion configured to allow the rod to slide through the ball and socket connection even when the mobile portion is pivoted in relation to the aiming tube.

According to another feature, the instrument further comprising a lock slidably disposed along the aiming tube, the lock having a forward position and being configured to fix the mobile portion of the guide tube at a selected pivot angle when the lock is disposed in the forward position.

According to another feature, the mobile portion comprises a serration configured to increase the maximum pivot angle at which the mobile portion of the guide tube can be fixed by the lock and to provide a pre-determined pivot angle.

According to another feature, the serration is configured for engagement with the lock without disposing the lock in the forward position, said engagement establishing a pre-determined pivot angle and preventing pivoting of the mobile portion.

According to another feature, the handling end of the instrument comprises a handle configured to allow the manipulation of the instrument and to facilitate the implantation of the intersomatic cage between the vertebrae.

Another objective of the preset invention is to propose a method for implanting a transforaminal intersomatic cage according to the invention into the disc space with an instrument according to the invention.

This objective is reached by a method for implanting an intersomatic cage for an intervertebral fusion graft into the disc space between adjacent vertebrae of a vertebral column, said disc space comprising an annulus and a nucleus, said method comprising the steps of:
- providing an intersomatic cage for an intervertebral fusion graft comprising a body generally defining an arc, the body comprising:
  - a lateral concave surface,
  - a lateral convex surface,
  - a substantially transverse upper surface,
  - a substantially transverse lower surface,
  - an end wall at a first longitudinal extremity of the body, the end wall comprising an end hole configured to receive a retaining end of a rod of an implantation instrument and oriented substantially tangential to the arc defined by the body, and
  - an incurvate return part at a second longitudinal extremity of the body opposite the end wall, the return part comprising a return hole oriented substantially tangential to the arc defined by the body and configured to receive an end portion of an implantation instrument;
- providing an instrument comprising:
  - a rod comprising a retaining end configured for insertion in the end hole,
  - a gripping end for gripping the intersomatic cage, the gripping end comprising a support spatula comprising a base and generally defining an arc complementary to the arc defined by the body, the support spatula comprising an end portion distal from the base configured for insertion into the return hole of the intersomatic cage, and
  - a guide tube in which the rod is slidably disposed and to which the base of the support spatula is mounted, the guide tube comprising an opening through which the retaining end of the rod can transit for insertion in the end hole, and
  - a handling end for manipulating the instrument;

making an incision to access the vertebral column;

incising the annulus and removing the nucleus from the disc space;

inserting the end portion of the spatula into the return hole of the intersomatic cage;

disposing the arc defined by the body proximal to the arc defined by the spatula;

fixing the intersomatic cage onto the instrument by inserting the retaining end of the rod into the end hole;

disposing the intersomatic cage in the disc space in an arcing movement;

releasing the intersomatic cage from the instrument by removing the retaining end of the rod from the end hole;

removing the instrument from the disc space; and suturing the annulus and the skin.

According to another feature, the step of disposing the intersomatic cage in the disc space is preceded or accompanied by a step of articulating a mobile portion of the instrument to a selected angle, said step of articulating the mobile portion being followed by a step of locking the mobile portion at the selected angle.

According to another feature, the step of disposing the intersomatic cage in the disc space is followed by the steps of determining the position and orientation of the intersomatic cage in the disc space by detecting a radio-opaque marker comprised in the body of the intersomatic cage with x-rays and, if such position or orientation is improper, adjusting the position or orientation of the intersomatic cage in the disc space.

According to another feature, the steps of inserting the end portion of the spatula into the return hole of the intersomatic cage and disposing the arc defined by the body proximal to the arc defined by the spatula are followed by, and the step of fixing the intersomatic cage onto the instrument by inserting the retaining end of the rod into the end hole is preceded by, a step of engaging a pin of the instrument with a recess disposed on the end wall of the intersomatic cage.

According to another feature, the step of disposing the intersomatic cage in the disc space is preceded by a step of distraction of the adjacent vertebrae.

BRIEF DESCRIPTION OF THE DRAWINGS

Other features and advantages of this present invention will appear more clearly on reading the description that follows, provided with reference to the appended drawings, in which.

DETAILED DESCRIPTION OF THE EMBODIMENTS

Figure 1A:
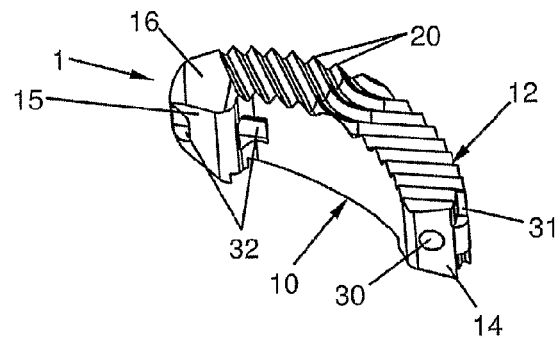
FIGS. 1A, 1B, 1C and 1D are views in perspective of the intersomatic cage according to various embodiments of the invention.

This present invention concerns a transforaminal intersomatic cage for an intervertebral fusion graft. This cage is used to maintain a disc space that is sufficient to allow a graft to be inserted into the disc space in order to grow and to allow an osseous fusion (arthrodesis) of the adjacent vertebrae. This cage is called transforaminal since it is particularly suitable to be implanted through the transforaminal approach, although it can also be implanted by any approach to suit the convenience of the surgeon responsible for the implantation. In a manner which is already known, this intersomatic cage has a body (1) in the shape of a circular arc having a lateral concave surface (10), a lateral convex surface (11), a straight upper surface (12), and a straight lower surface (13). The body (1) therefore has more or less the shape of a banana or simple bracket, and therefore does indeed describe a circular arc.

This circular arc shape of the cage according to various embodiments of the invention is particularly well-matched to the shape of the edges of the vertebral plates, which allows the cage to be positioned in the vicinity of the periphery of the vertebral plates, that is to say on their most solid portion. A cage according to various embodiments the invention will therefore be implanted at the level of the anterior peripheral portion of the vertebral plates, for example. This positioning of the cage close to the edges of the vertebral plates also enables to obtain a large initial surface for an osseous graft or a substitute. At one of the extremities of the body (1), the cage includes an end wall (14) having at least one hole (30), called the end hole, designed to receive a rod (53) of an instrument (5) for implantion of the cage between the vertebrae.

In a particularly advantageous embodiment of the cage according to the invention, the end hole (30) has an orientation that is more or less tangential to the circular arc described by the body (1). This orientation of the end hole (30) tangentially to the circular arc described by the body (1) facilitates the thrusting of the cage by the cage implantation instrument (5) and facilitates the insertion and withdrawal of the rod (53) of this instrument (5), respectively, into and out of the end hole (30). Moreover, this end wall (14) includes at least one recess (31) designed to receive at least one pin (54) of a cage implantation instrument (5). This recess (31) is used to provide an additional surface for the gripping of the cage by the instrument. It can consist of a simple shoulder or a recess of more complex shape such as, for example, a recess with a groove in which a serration of the pin (54) (thus having the shape of a spur, for example) of the instrument (5) can be locked.

In a particularly advantageous embodiment of the cage according to the invention, the extremity opposite to the end wall (14) of the body (1) includes a return part (15) extending the body (1) toward the centre of the circle on which the circular arc described by the body (1) lies. This return part provides better stability of the intersomatic cage between the vertebrae without increasing its dimensions excessively. This return part is used to prevent the intersomatic cage from tilting to one of its sides under the effect of the stresses to which it is subjected when implanted between two vertebrae of a patient. Moreover, this return part (15) includes at least one hole (32), called the return hole, whose orientation is more or less tangential to a circular arc defined by the concave surface (10) of the body (1) and designed to receive at least one end portion (55) of a cage implantation instrument (5). Thus, the instrument (5) can include a spatula (56) having a shape complementary to that of the circular arc described by the body. This spatula (56) thus hugs the shape of the cage by fitting its body (1). At one end of the spatula (56), an end portion (55) can be designed for insertion into this return hole (32). The fitting together of the end hole (30), the recess (31) and the return hole (32) with the rod (53), the pin (54) and the end portion (55) of the cage implantation instrument (5) respectively, ensures a good grip on the cage by the instrument (5) when one end of the rod (53) is placed in the end hole (30). This complete gripping of the cage up to the most distal end facilitates the implantation of the cage by providing good stability of the cage at the end of the instrument (5). This good stability is also particularly important in the case of implantation through the transforaminal approach. The rod (53) is designed to slide in the instrument (5) so that it can be withdrawn from the end hole (30) and to allow freeing of the cage and withdrawal of the instrument (5).

Figure 1B:
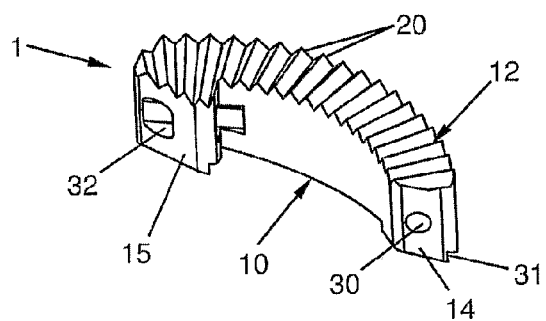
Figure 1C:
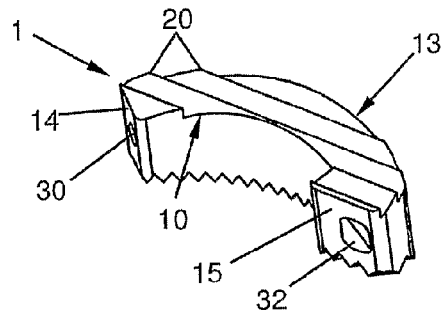
Figure 1D:
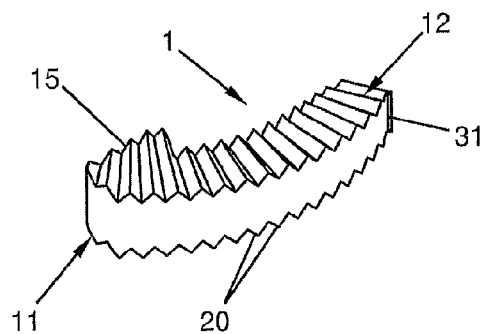

In a manner which is already known, at least one of the upper and lower surfaces of the body (1) is equipped with serrations (20) that oppose the movement of the cage in relation to the adjacent vertebrae between which it is implanted. The invention provides for different possible orientations of the serrations (20). In an advantageous manner, in one embodiment of the invention, the serrations (20) present on two opposite surfaces of the cage may not have the same orientation, so as to oppose the movement of the cage in different directions for each of the faces, as can be seen particularly in FIGS. 1A to 1C. In another embodiment, the serrations (20) present on two opposite surfaces of the cage will have the same orientation, as can be seen particularly in FIG. 1D. Likewise, serrations (20) present on one surface of the cage can have an orientation that is different from other serrations located on the same surface. Conversely, all the serrations (20) present on a given surface of the cage can have the same orientation. Depending on the embodiment, the intersomatic cage can therefore include any combination of these orientations on all or part of either of its surfaces. The extremities of the circular arc described by the body (1) define a longitudinal axis of the cage. The cage has larger dimensions on this longitudinal axis than on the axis perpendicular to it. This longitudinal axis will allow the different possible orientations of the serrations to be defined. Thus in one embodiment, at least one part of the serrations (20) can be oriented parallel, as can be seen particularly in FIG. 1C, or perpendicular to this longitudinal axis of the cage. In another embodiment, they can be oriented so as to form an angle of between 0 and 90 degrees in relation to this longitudinal axis of the cage. In another embodiment, at least one part of the serrations (20) can describe chevrons that are centred in relation to an axis perpendicular to this longitudinal axis, as can be seen particularly in FIG. 1A. In another embodiment, at least one part of the serrations (20) can describe concentric circular arcs, each with, in relation to the circular arc described by the body (1), an axial symmetry whose axis of symmetry is parallel to this longitudinal axis of the cage. In another embodiment, at least one part of the serrations (20) will be oriented parallel to radii defined by the circle on which the circular arc described by the body lies (1), as can be seen particularly in FIGS. 1B and 1D.

Furthermore, the return part (15) includes upper and lower surfaces extending the upper and lower surfaces respectively of the body (1). In one embodiment, at least one of these upper and lower surfaces of the return part (15) can also be equipped with serrations (20) that oppose the movement of the cage. In another embodiment, at least one of these upper and lower surfaces of the return part (15) can include at least one chamfer (16) facilitating the insertion of the cage in the disc space, as can be seen particularly in FIG. 1A.

In the embodiments shown in the figures, the upper and lower surfaces of the cage (1) are generally flat and the mean planes defined by these upper and lower surfaces are substantially parallel to each other. In some embodiments (not shown) of the present invention, the mean planes defined by the upper and lower surfaces of the cage (1) are not parallel to each other. These planes may thus form an angle allowing to correct defects of the spine (orientation of the vertebrae). In such embodiments, the cage (1) can impose a lordosis when implanting between the vertebrae. Since several cages (1) can be used together within a single intervertebral space, such embodiments allow correcting defects of the spine in any orientation, because any combination of cages (1) with different angles between their upper and lower surfaces can be used.

Figure 5A:
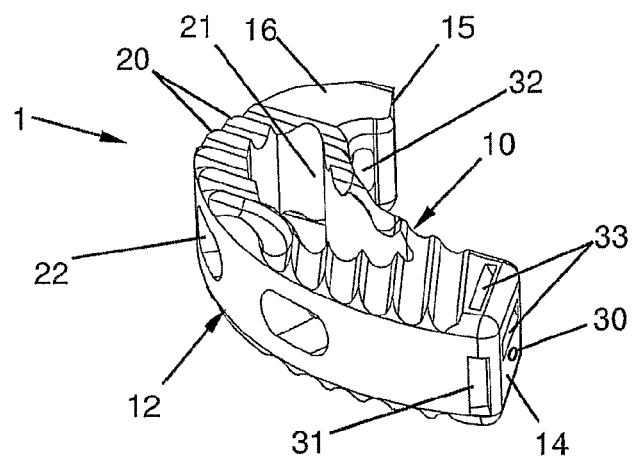
FIGS. 5A and 5B provide views in perspective of two different embodiments of the intersomatic cage according to the invention and FIG. 5C provides a top view of another embodiment of the intersomatic cage according to the invention.
Figure 5B:
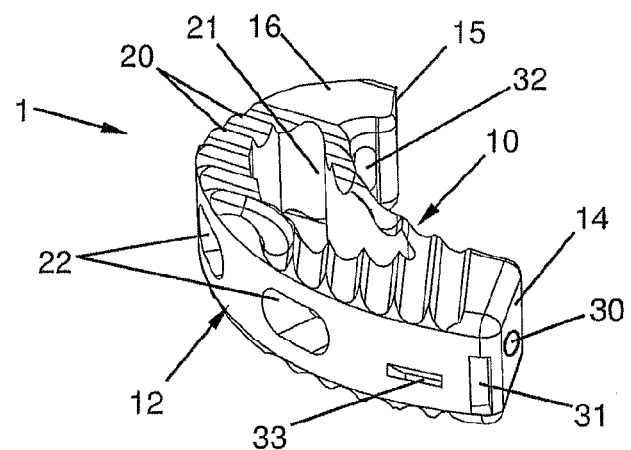
Figure 5C:
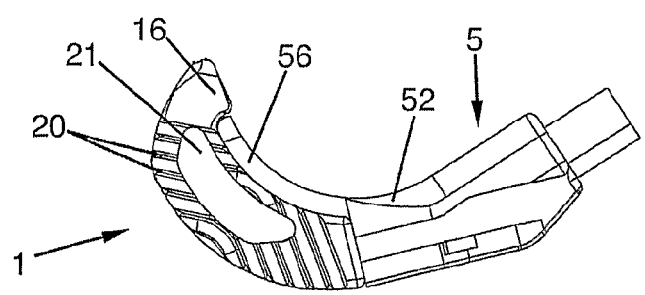
Figure 6A:
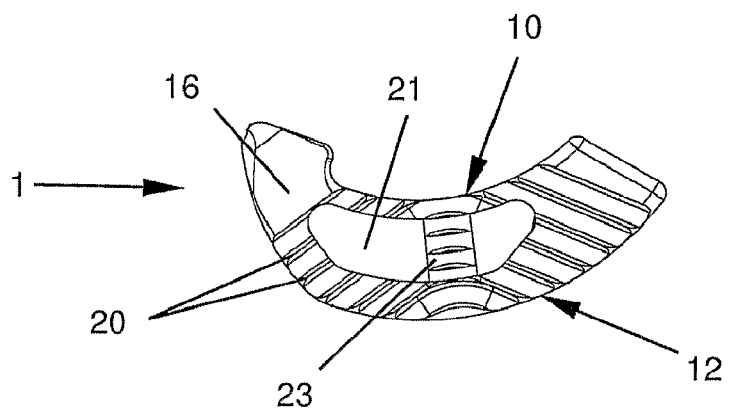
FIG. 6A provides a top view of another embodiment of the intersomatic cage according to the invention and FIGS. 6B and 6C provide, respectively, a top view and a side view, of an anchor according to another embodiment of the present invention.

In some embodiments of the present invention, as particularly shown in FIGS. 5A to 5C and 6A, at least one of the surfaces of the cage comprises at least one opening (21 or 22). As shown on the figures, the cage (1) can comprise such openings (21) located on its upper and/or lower surfaces and can also comprise such openings (22) on at least one of its side surfaces (10, 12). In various embodiments, such opening (21, 22) may form a blind hole or may form a conduit through the body of the cage. Such openings allow securing the cage onto the vertebrae by enabling a bony graft or substitute to grow inside the opening. The bony graft or substitute may thus be inserted inside the opening (21 or 22) or may be simply placed in the intervertebral space and grow inside the opening. In particular when the cage comprises an opening (21) forming a conduit extending from the upper surface to the lower surface, it can be advantageous that the cage (1) further comprises a crosspiece (23) passing through the opening (21) for consolidating the cage (1), as shown in FIG. 6A.

Figure 6B:
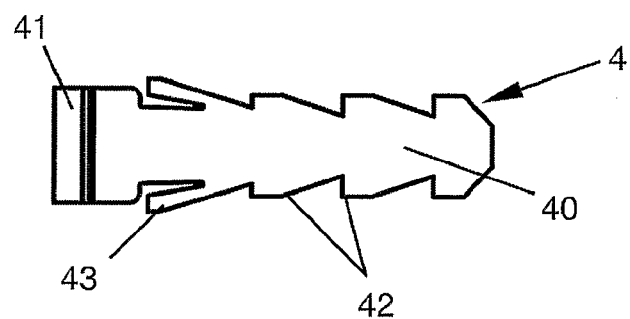
Figure 6C:
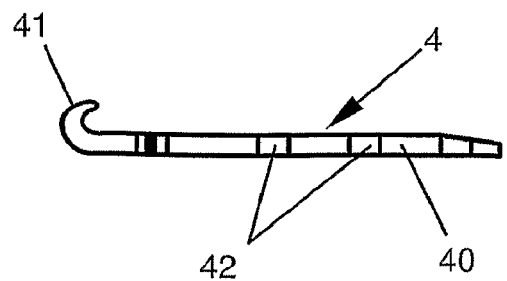

In some embodiments of the present invention, the cage comprises at least one slit (33) passing through the body of the cage (1) and extending form at least one of the surfaces of the cage to another, that is to say the upper surface and/or lower surface and/or the end wall and/or the concave surface (10) and/or the convex surface (12) and/or one surface of the return part (15). As shown in FIG. 5A, the slit (33) may, for example, extend form the end wall (14) to the upper surface of the cage but may extend from the convex surface (12) to the lower surface of the cage as shown in FIG. 5B. This slit (33) is intended to receive an anchor (4), intended to be impacted into the vertebral bodies. As shown in FIGS. 6B and 6C, the anchor (4) comprises a substantially rectangular flat plate (40) intended to enter the slit (33) and be impacted in the vertebral body, thus enabling the anchoring of the cage (1) in the vertebra. The slit (33) is thus a conduit through the body of the cage (1) and may have a rectangular section adapted to receive the anchor (4). The anchor plate (40) can comprise notches (42) oriented to retain the anchor (4) in a vertebra. In a variant embodiment, the anchor plate (40) can comprise at one of its end, a chamfer or bevel (visible in FIG. 6C) for facilitating its penetration into the vertebral bodies. In a variant embodiment, at the end opposite the end that may comprise the chamfer, the anchor plate (4) may comprises a return part (41) for securing the anchor onto the cage (1). This return part (41) may consist in a curved section, as shown in FIG. 6C, which may be interlocked onto an edge of the opening of the slit (33) on one surface of the body. In a variant embodiment, the edge of the slit (33) may comprise a groove for facilitating the interlocking of the return part (41) of the anchor (4). In a variant embodiment, the anchor (4) comprises, close to the return part (41), flexible tabs (43) oriented towards the return part (41) of the anchor (4). In this variant, these flexible tabs (43) are configured to fold back against the edges of the anchor plate (40) to permit the insertion of the anchor (4) into the slit (33) of the cage (1). In this embodiment of the anchor (4), the inner walls of the slit (33) of the cage (1) comprise recesses for receiving the flexible tabs (43) and securing the anchor (4) into the cage (1). In this embodiment, the return part (41) of the anchor (4) may consist simply, for example, in an enlargement of the anchor plate (40) forming a stop cooperating with the surface of the cage on which the slit is located. Depending on the embodiment chosen, the orientation of the slit (33), and thus of the anchor (4) inserted in it, may form an angle between 5° and 85° relative to the upper or lower surface of the cage. The cage (1) may comprise several slits (33) for the insertion of several anchors (4), with similar or different angles. Furthermore, the various embodiments of the slits (33) and anchors (4) described here can used in any embodiment of the cage (1), irrespective of its shape (angle between the upper and lower surfaces) or the presence or absence of openings (21 and/or 22).

This present invention also concerns an instrument (5) for the implantation of an intersomatic cage between the vertebrae. This instrument according to the invention is particularly suitable for implantation, through the transforaminal approach, of an intersomatic cage for an intervertebral fusion graft, although it could naturally be used for any approach that is convenient for the surgeon responsible for the implantation. The instrument (5) is designed to be particularly suitable for use in combination with the intersomatic cage described previously. The instrument (5) according to an embodiment of the invention includes an extremity for gripping the cage allowing the cage to be held at the end of the instrument and called the gripping end. The extremity of the instrument opposite its gripping end allows the manipulation of the instrument by the surgeon and is called the handling end. The gripping end of the instrument (5) includes at least one tube (52), called the guide tube. At the extremity of this guide tube (52), on one edge of the latter, is mounted a spatula (56), called the support spatula. This spatula (56) has the shape of a circular arc, designed to at least partially fit onto the circular arc described by the body (1) of the cage. By hugging the shape of the body (1), this spatula provides the cage with solidity. The spatula will therefore protect the cage in particular against impact, to which it is sometimes less resistant than to pressures. At the base of the support spatula (56), the guide tube (52) includes an opening through which one end of the rod (53) passes to fit into the end hole (30) of the cage. This rod (53) is mounted to slide in the guide tube (52) and has a shape and dimensions that make it suitable to be inserted into the end hole (30) of the cage, so as to allow the cage to be gripped. In one embodiment, this rod (53) extends up to the vicinity of the handling end of the instrument (5). The rod (53) includes at least one button (61) projecting through a groove (610) on at least one edge of the instrument (5), this button (61) allowing the rod to be slid (53) and its position to be adjusted in relation to the opening present at the end of the guide tube (52) holding the support spatula (56). This button will preferably be located at the extremity of the rod (53) and, according to the embodiment, can therefore be located close to the handling end of the instrument (5) or anywhere on the instrument, although it would obviously be more practical, in principle, that it should be close to the handling end.

In one embodiment, the guide tube (52), at the end on which the support spatula is mounted (56) but on the opposite edge, includes at least one pin (54) whose shape and dimensions are suitable to fit onto at least one recess (31) present on the end wall (14) of the cage. This embodiment is particularly suitable for the one of the embodiments of the cage presented above and improves the quality of the grip on the cage by the instrument (5).

In one embodiment, the support spatula (56), at the end opposite to the guide tube (52), includes at least one end portion (55) whose shape and dimensions make it suitable to be inserted into at least one hole (32), called the return hole, present on a return part (15) of the cage. This embodiment is particularly suitable for the one of the embodiments of the cage in which a return part (15) extends the body (1) toward the centre of the circle on which the circular arc described by the body (1) lies. Since this return hole (32) has an orientation that is more or less tangential to a circular arc defined by the concave surface (10) of the body (1), the end portion (55) at the end of the spatula (56) in a circular arc will therefore have a shape that is particularly suitable to fit into the return hole (32). In one embodiment that combines the resources for fitting together the instrument and the cage, described above, with the fitting together of the rod (53), the pin (54) and the end portion (55) of the cage implantation instrument (5) to the end hole (30), the recess (31) and the return hole (32) respectively of the cage, ensures a good grip on the cage by the instrument (5) when one end of the rod (53) is placed in the end hole (30), and facilitates the implantation of the cage.

Figure 3A:
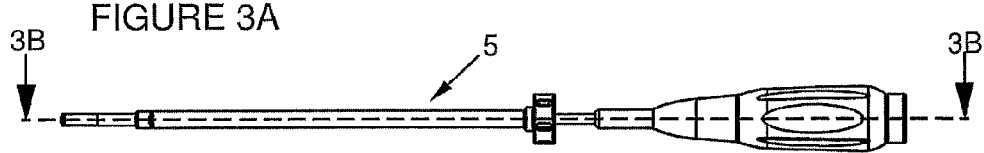
FIG. 3A provides a top view of one embodiment of the instrument for implanting an intersomatic cage with a plane section 3B-3B, with FIG. 3B showing a view in section according to axis 3B-3B of this embodiment of the insertion instrument, and FIGS. 3C and 3D showing the detail of the portions indicated, respectively, by circles 3C and 3D in FIG. 3B.
Figure 3B:
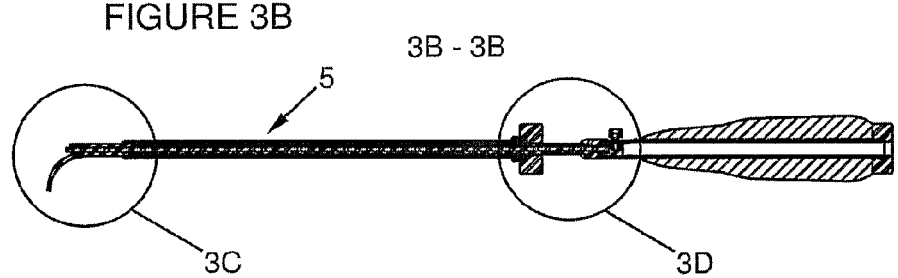
Figure 3C:
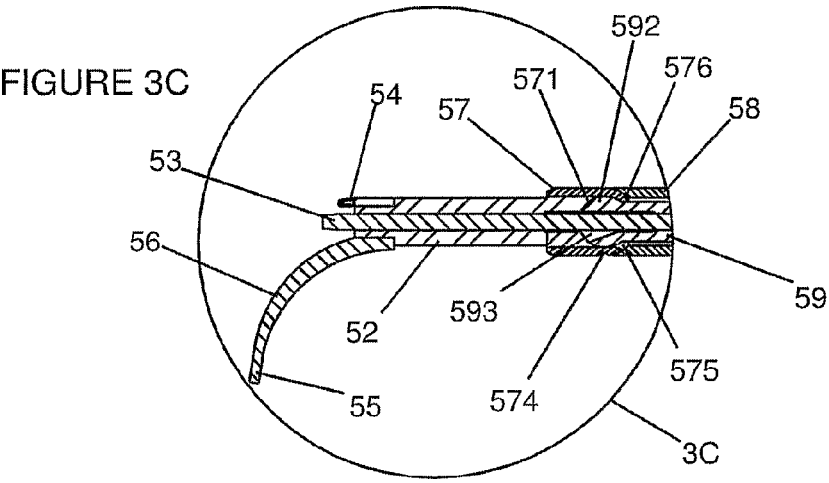
Figure 3D:
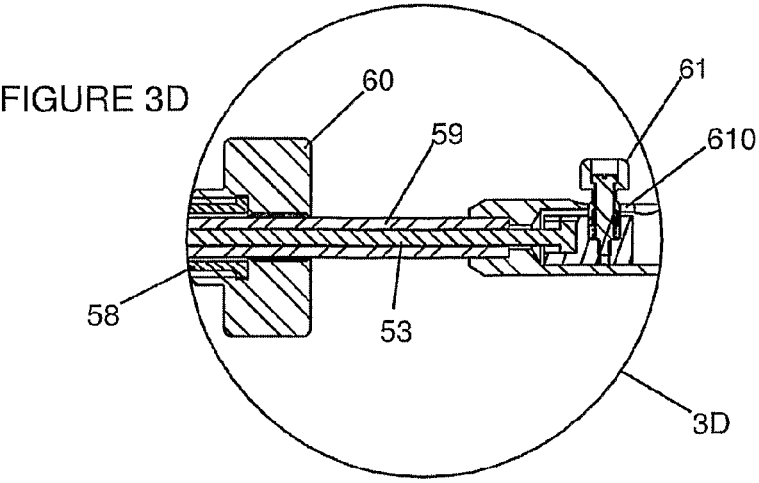
Figure 4A:
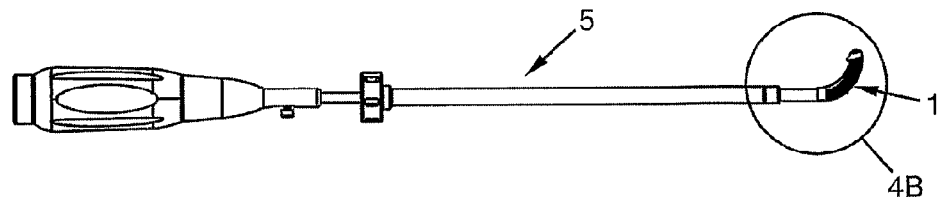
FIG. 4A provides a view in profile of one embodiment of the instrument for implanting an intersomatic cage with a method for insertion of the intersomatic cage held at the gripping end of the instrument, with FIG. 4B showing the detail of the portion indicated by circle 4B in FIG. 4A, and FIG. 4C showing a top view of this embodiment of the instrument holding the intersomatic cage, with a plane section 4D-4D, where FIG. 4D provides a view in section according to axis 4D-4D of this embodiment.
Figure 4B:
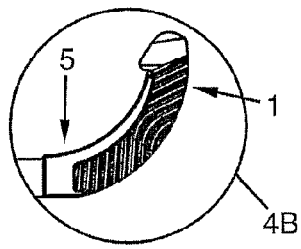
FIG. 4E shows the detail of the portion indicated by circle 4E in FIG. 4D.
Figure 4C:
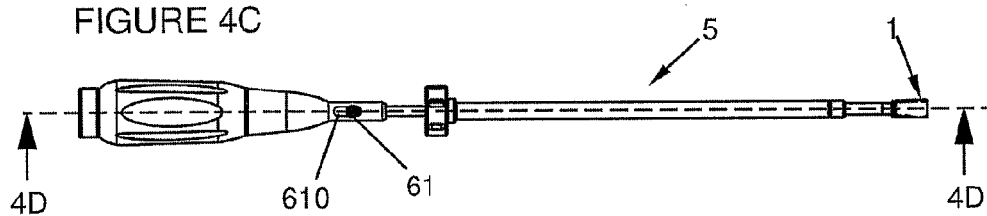
Figure 4D:
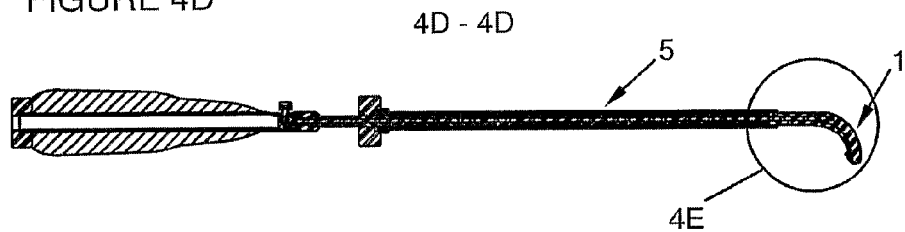
Figure 4E:
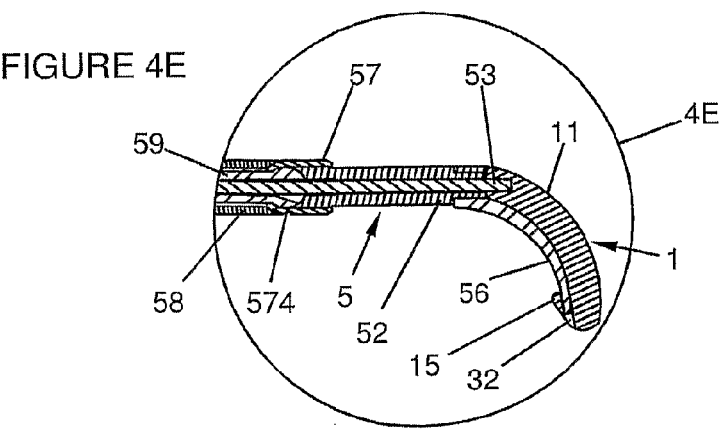

In a particularly advantageous embodiment and suitable for the transforaminal approach, the guide tube (52), at the end opposite to that holding the support spatula (56), includes a mobile portion (57) that pivots in relation to a tube (59), called the aiming tube, extending up close to the handling end of the instrument (5). This mobile portion (57) pivots in at least one direction that is more or less parallel to the orientation of the circular arc defined by the support spatula (56). As can be seen particularly in FIG. 3C, the mobile portion (57) and the aiming tube (59) together can form a ball and socket connection (or swivel link), one of them having one end in the form of a ball or sphere (592) and the other having a hollow end forming a socket, called spherical recess (571), whose shape and dimensions are complementary to those of this sphere. In the embodiment illustrated in FIG. 3C, one end of the aiming tube (59) has a shape of sphere (592) and the corresponding end of the guide tube (52) forms a spherical recess. In one embodiment of the invention, at least the edge (575) of the spherical recess (571) located on the same side of the instrument (5) as the support spatula (56), in the ball and socket connection formed by the mobile portion (57) and the aiming tube (59), encompasses the sphere to a lesser extent than the other edges (576) of this recess (571), so as to allow pivoting at least in a direction that is more or less parallel to the orientation of the circular arc defined by the support spatula (56).

Figure 2A:
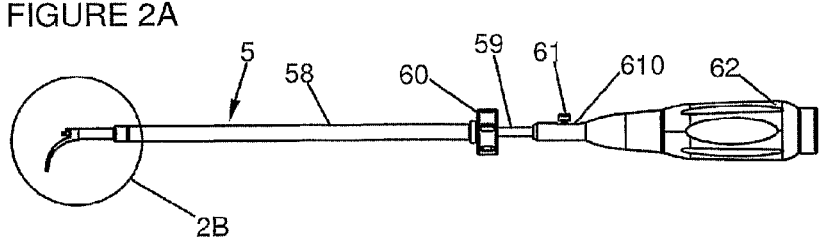
FIGS. 2A and 2C are views in profile of one embodiment of the instrument for implanting intersomatic cage between the vertebrae, with the gripping end of the instrument in position, respectively straight and angled, with FIGS. 2B and 2D showing the detail of the portions indicated by circles 2B and 2D respectively in FIGS. 2A and 2C respectively.
Figure 2B:
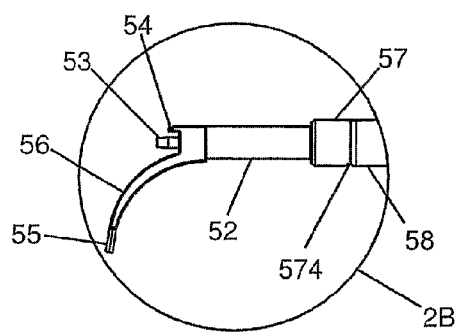
Figure 2C:
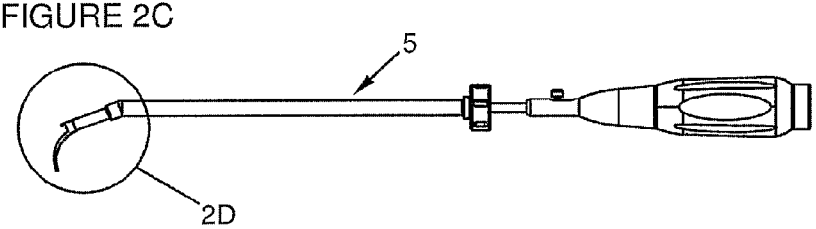
Figure 2D:
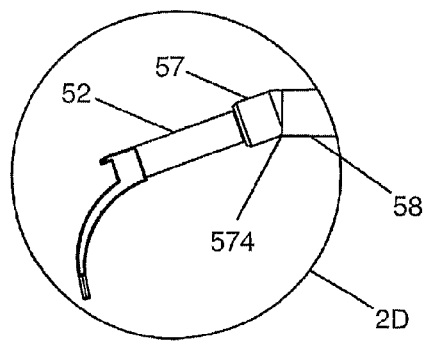

In one embodiment, the rod (53) is flexible, and traverses the ball and socket connection at its centre. The sphere (592) then has a channel at its centre to allow the rod to slide (53). This channel will be hollowed out at least on its edge located on the same side of the instrument (5) as the support spatula (56). Thus, the channel will include a hollowed out portion (593) allowing the rod (53) to slide through the ball and socket connection even when the instrument (5) is in its angled position due to pivoting of the ball and socket connection, as illustrated in FIGS. 2C and 2D.

In one embodiment, a locking tube (58) is screwed onto the aiming tube (59) and includes a locking ring (60) that allows the locking tube to be screwed in (58). Screwing-in and unscrewing allows the forward and backward motion of the locking tube (58) in relation to the aiming tube (59). The forward motion of the locking tube (58) results naturally in bringing the locking tube (58) into contact with the mobile portion (57) and, as a consequence, prevents the pivoting of the mobile portion (57). Thus, the guide tube (52) can be locked in relation to the aiming tube (59), at any angle between the guide tube (52) and the aiming tube (59). The mobile portion (57) that pivots in relation to the aiming tube (59) can also, in one embodiment, include at least one serration (574), particularly visible in FIG. 3C. The presence of this serration (574) allows pivoting of the mobile portion (57) through a larger amplitude than if the mobile portion entered directly into contact with the locking tube (58). This serration (574) allows to obtain a particular angle formed by the angled portion between the support tube (52) and the aiming tube (59). Moreover, in one embodiment, this serration (574) can be designed so that when the guide tube (52) forms a given angle with the aiming tube (59), one edge of one end of the locking tube (58) locks into this serration (574), as illustrated in FIGS. 2A to 2D. This serration (574) is therefore used to stop the pivoting and to maintain the instrument in at least one position until it is totally immobilised by screwing-in of the locking tube (58).

In a manner which is already known, the handling end of the instrument (5) can naturally be fitted with a handle (62) allowing the manipulation of the instrument (5) and facilitating the implantation of the cage between the vertebrae by allowing effective thrust to be applied to the instrument (5).

As mentioned previously, the intersomatic cage and the instrument according to this present invention are particularly suitable for implantation of the cage between two adjacent vertebrae using the transforaminal approach. This implantation can be performed as described below, although other procedural variants can naturally exist, and the surgeon can naturally adapt the technique described here at his convenience, in accordance with any changes in the techniques employed conventionally for example. In particular, this present invention can be used in combination with osseous anchor implants, connected together by immobilising bars, allowing the movement of the two adjacent vertebrae, between which the cage is designed to be inserted, to be eliminated or limited. These osseous anchor implants can consist, for example, of those described in the international patent applications submitted by this present applicant and published under the numbers WO02/080788(A1), WO03/049629(A1) and WO2005/020829(A1) or by any other type of resources for immobilisation of the adjacent vertebrae. The procedure relating to the joining of the adjacent vertebrae is specific to the resources used to immobilise the adjacent vertebrae and therefore need not be described here.

Only the procedure used during an implantation through the transforaminal approach will be detailed here, the implantation by other approaches being relatively similar but easier, in particular because of the fact that the transforaminal approach needs to bypass the articular processes. The procedure for implantation through the transforaminal approach begins naturally by at least one incision laterally to the axis of the vertebral column. Preferably, two intermuscular incisions will be made, along a path that is well known to the professional surgeon for example, as described by Dr Wiltse. According to the size of the cage chosen and/or according to the space between the two vertebrae, a resection, at least partial, of the articular processes can be effected in order to improve access to the foramen and to the disc space. These articular processes will then preferably be resected laterally, on the side for insertion of the cage. If an intra-articular graft is desired, an opening and an avivement (withdrawal of the cartilage) of the articular processes, at least on one side but possibly on both sides, will allow the insertion of at least one intra-articular graft. The insertion of the osseous anchor implants designed to immobilise the two adjacent vertebrae can be effected at this stage of the procedure. These osseous anchor implants screwed into each of the adjacent vertebrae and connected together by a bar, here allow a first posterior distraction in order to facilitate access to the disc space. A tool of known type such as a nerve root retractor (or root spreader) can be used to protect the roots of the vertebrae. A lateral incision in the external layer of the annulus, between the transverse articular processes for example, will provide access to the disc space. In a manner which is already familiar, the formation of an open flap, held by suspension ties for example, will facilitate the following operations. Then the surgeon will proceed to the complete removal of the nucleus and of the internal layers of the annulus. Different tools of known types, such as an angled disc clamp, curettes and rasps (straight and angled) will be used at this stage to prepare the disc space and withdraw the cartilage from the vertebral plates without damaging or weakening it.

At this stage of the procedure, the surgeon will have cleared access to the disc space. The osseous anchor implants will allow the surgeon to spread the vertebrae so as to facilitate insertion of the cage. For example, the surgeon will use osseous anchor implants screwed into the vertebrae and connected together by a bar parallel to the axis of the vertebral column. The osseous anchor implants generally include screws driven into the vertebrae and defining a longitudinal securing axis. At this stage, these longitudinal axes of the osseous anchor implants are not parallel to each other but cross in front of the vertebral column. Together with the axis of the bar, these axes form an inverted capital A. The surgeon will then adjust the spread of the osseous anchor implants. To this end, the surgeon can position spreader tubes on the heads of the osseous anchor implants in order to spread these as much as possible or can use distraction forceps of a known type, for example. In the case of osseous anchor implants having a mobile head (called polyaxial head), as disclosed, for example, in the patent application number WO2005/020829(A1), the surgeon will then screw in the head of these osseous anchor resources on the bar to fix their position along the bar parallel to the axis of the vertebral column. The osseous anchor implants thus implanted and held securely on the bar will allow an anterior distraction to be performed, thanks to the mobility of the head in relation to the bar. The surgeon applies pressure to the spreader tubes so as to move them toward each other, which tends to open the inverted capital A at its base, so that it becomes a capital H. In the case of osseous anchor implants having a fixed head, as disclosed, for example, in the patent application number WO03/049629(A1), the surgeon will use the distraction forceps to maintain the gap between the osseous anchor implants without screwing in the head of these osseous anchor resources on the bar. Even if the bar is fixed with a fixation screw having a ball and socket connection at its base, as disclosed in the application WO03/049629(A1), such screwing in would indeed result in blocking the head of the osseous anchor implants on the bar. The surgeon thus should rather maintain the gap between the osseous anchor implants with distraction forceps placed between the heads of the two osseous anchor implants screwed in each of the vertebrae. Then, The surgeon applies pressure to the spreader tubes so as to move them toward each other, which tends to open the inverted capital A at its base, so that it becomes a capital H because of the presence of the distraction forceps. This operation can possibly be repeated several times. For example, in the case of osseous anchor implants with polyaxial head, the operation may be repeated by unscrewing the heads of the osseous anchor implants from the bar and separating the spreader tubes to spread the heads and then screwing in the heads of the implants and drawing together the spreader tubes to spread the feet of the capital H, thus opening the disc at the front. This anterior opening of the disc space can be accompanied by an adjustment of the lordosis.

The surgeon will then proceed to the choice of the cage to be implanted, using trial cages with the same dimensions as the cages designed to be implanted. A trial cage is placed on the instrument (5) and is then impacted into the disc space. Impaction should be effected without excessive force in order not to weaken (damage) the vertebral plates. The trial cage is removed using a tool of known type such as an extraction masselotte (or extractor or removal masselotte or bobweight), and this operation can be repeated until a cage of satisfactory size has been found.

The definitive cage can then be placed on the implantation instrument (5) by inserting the end portion (55) of the spatula (56) into the return hole (32) of the cage and moving the circular arc of the body (1) in relation to the spatula (56) until the pin (54) locks into the recess (31) of the end wall (14). The cage is then locked onto the instrument (5) by means of the sliding rod (53) which enters into the end hole (30). Articulation of the instrument at its distal part by means of the mobile portion (57) allows the most appropriate angle to be found for engagement of the cage in the intersomatic space. The angle can be locked by the screwing in the locking tube (58) using the threaded ring (60) for example by means of a tool of known type such as a pin wrench. The cage thus held on the instrument and oriented in an optimal manner can then be impacted between the vertebrae. The cage will preferably be impacted as anteriorly as possible, in a circular movement. In order to optimise the positioning of the cage, the angle of the articulation formed by the mobile part (57) can be adjusted during impaction, taking care to correctly lock this angle by means of the locking ring (60). The position and the orientation of the cage in the intersomatic disc space can then be verified by means of an x-ray appliance of known type, such as a brightness amplifier for example. In fact, in one embodiment the cage includes at least one radio-opaque marker which will be detected by the brightness amplifier. The surgeon can then adjust the positioning of the cage according to the position and the orientation of the marker or markers. When the cage has been correctly implanted, it will be released from the instrument (5) by moving the sliding rod (53) in the direction of the handling end. The surgeon then only has to position the osseous graft(s) or substitute(s) between the cage (preferably placed at the level of the anterior edges of the vertebral plates) and the medulary cavity. To this end, the surgeon will use a tool of known type, such as a spatula for example. The flap formed in the external layer of the annulus can then be re-closed and sutured, so as to maintain the graft in place. A graft, of the posterolateral type for example, can be effected at this stage in order to optimise the joining together of the vertebrae. Graft will be then placed on the transverse articular process for example. A redon drain can possibly then be put in place, and a subcutaneous suturing followed by a cutaneous suturing of the incisions will allow the surgical procedure to be finalised.

It should be obvious to people well versed in these techniques that this present invention allows embodiments in many other specific forms without the moving outside the spirit and scope of the invention as claimed and that it allows any combination of non-exclusive embodiments enclosed herein. As a consequence, the present embodiments should be considered as illustrations only, but can be modified within the domain defined by the reach of the attached claims, and the invention must not be limited to the details given above.

The invention claimed is:

1. An intersomatic cage for an intervertebral fusion graft comprising a body generally defining an arc, the body comprising: a lateral concave exterior surface; a lateral convex exterior surface; a substantially transverse upper exterior surface; a substantially transverse lower exterior surface; an end wall at a first longitudinal extremity of the body, the end wall comprising an end hole configured to receive a retaining end of a rod of an implantation instrument and oriented substantially tangential to the arc defined by the body; an incurvate return part protruding externally from the lateral concave exterior surface at a second longitudinal extremity of the body opposite the end wall; and at least one conduit extending longitudinally from either the lateral convex or the lateral concave exterior surface to either the upper or the lower exterior surface, the conduit having a generally rectangular transverse cross section and being configured to house an anchor comprising a flat anchor plate.

2. An intersomatic cage according to claim 1, wherein the end wall comprises a recess configured to receive a pin of an implantation instrument.

3. An intersomatic cage according to claim 1, wherein the return part comprises a return hole oriented substantially tangential to the arc defined by the body and configured to receive an end portion of an implantation instrument.

4. An intersomatic cage according to 3, wherein the end wall comprises a recess configured to receive a pin of an implantation instrument, the end hole, the recess, and the return hole being configured to cooperate with, respectively, a retaining end of a rod, a pin, and an end portion of an implantation instrument, to secure a grip on the intersomatic cage by the implantation instrument.

5. An intersomatic cage according to claim 1, wherein at least one of the upper and lower exterior surfaces of the body comprises serrations oriented to oppose the movement of the intersomatic cage following intervertebral implantation of the intersomatic cage.

6. An intersomatic cage according to claim 5, wherein the first and second longitudinal extremities of the body define a longitudinal axis of the intersomatic cage, and at least some of the serrations are oriented substantially parallel to the longitudinal axis of the intersomatic cage.

7. An intersomatic cage according to claim 5, wherein the first and second longitudinal extremities of the body define a longitudinal axis of the intersomatic cage, and at least some of the serrations are oriented substantially perpendicular to the longitudinal axis of the intersomatic cage.

8. An intersomatic cage according to claim 5, wherein the first and second longitudinal extremities of the body define a longitudinal axis of the intersomatic cage, and at least some of the serrations are disposed in a chevron configuration about an axis substantially perpendicular to the longitudinal axis of the intersomatic cage.

9. An intersomatic cage according to claim 5, wherein the first and second longitudinal extremities of the body define a longitudinal axis of the intersomatic cage, and at least some of the serrations define concentric circular arcs each being disposed symmetrically to the arc defined by the body, in relation to an axis of symmetry substantially parallel to the longitudinal axis of the intersomatic cage.

10. An intersomatic cage according to claim 5, wherein at least some of the serrations are oriented substantially normal to the arc defined by the body.

11. An intersomatic cage according to claim 5, wherein all of the serrations on the upper or lower exterior surface of the intersomatic cage have substantially the same orientation.

12. An intersomatic cage according to claim 5, wherein some of the serrations on the upper or lower exterior surface of the intersomatic cage do not have the same orientation as other serration on the same surface of the intersomatic cage.

13. An intersomatic cage according to claim 5, wherein serrations on each of the upper and lower exterior surfaces of the intersomatic cage have the same orientation.

14. An intersomatic cage according to claim 5, wherein the serrations on the upper exterior surface of the intersomatic cage have an orientation different from the orientation of the serrations on the lower exterior surface of the intersomatic cage.

15. An intersomatic cage according to claim 1, wherein the return part comprises upper and lower surfaces extending, respectively, from the upper and lower exterior surfaces of the body, at least one of the upper and lower surfaces of the return part comprising serrations configured to oppose the movement of the intersomatic cage following intervertebral implantation of the intersomatic cage.

16. An intersomatic cage according to claim 1, wherein the return part comprises upper and lower surfaces extending, respectively, from the upper and lower exterior surfaces of the body, at least one of the upper and lower surfaces of the return part comprising a chamfer configured to facilitate intervertebral implantation of the intersomatic cage.

17. An intersomatic cage according to claim 1, wherein the body comprises a radio-opaque marker configured to identify the intersomatic cage in x-ray images.

18. An intersomatic cage according to claim 1, wherein each of the upper exterior surface and the lower exterior surfaces define a mean plane, and the mean planes defined by the upper and lower exterior surfaces of the cage are substantially parallel to each other.

19. An intersomatic cage according to claim 1, wherein each of the upper exterior surface and the lower exterior surfaces define a mean plane, and the mean planes defined by the upper and lower exterior surfaces of the cage form an angle allowing to correct defects of the spine.

20. An intersomatic cage according to claim 1, wherein at least one of the surfaces of the cage comprises at least one opening allowing the growth of a bony graft or substitute.

21. The intersomatic cage of claim 1 in which the conduit comprises a lock for the anchor.

22. A method for implanting an intersomatic cage for an intervertebral fusion graft into the disc space between adjacent vertebrae of a vertebral column, said disc space comprising an annulus and a nucleus, said method comprising the steps of:
providing an intersomatic cage for an intervertebral fusion graft comprising a body generally defining an arc, the body comprising:
a lateral concave exterior surface,
a lateral convex exterior surface,
a substantially transverse upper exterior surface,
a substantially transverse lower exterior surface,
an end wall at a first longitudinal extremity of the body, the end wall comprising an end hole configured to receive a retaining end of a rod of an implantation instrument and oriented substantially tangential to the arc defined by the body,
an incurvate return part protruding externally from the lateral concave exterior surface at a second longitudinal extremity of the body opposite the end wall, the return part comprising a return hole oriented substantially tangential to the arc defined by the body and configured to receive an end portion of an implantation instrument; and at least one conduit extending longitudinally from either the lateral convex or the lateral concave exterior surface to either the upper or the lower exterior surface, the conduit having a generally rectangular transverse cross section and being configured to house an anchor comprising a flat anchor plate;
providing an instrument comprising:
a rod comprising a retaining end configured for insertion in the end hole,
a gripping end for gripping the intersomatic cage, the gripping end comprising a support spatula comprising a base and generally defining an arc complementary to the arc defined by the body, the support spatula comprising an end portion distal from the base configured for insertion into the return hole of the intersomatic cage, and
a guide tube in which the rod is slidably disposed and to which the base of the support spatula is mounted, the guide tube comprising an opening through which the retaining end of the rod can transit for insertion in the end hole, and
a handling end for manipulating the instrument;
making an incision to access the vertebral column;
incising the annulus and removing the nucleus from the disc space;
inserting the end portion of the spatula into the return hole of the intersomatic cage;
disposing the arc defined by the body proximal to the arc defined by the spatula;
fixing the intersomatic cage onto the instrument by inserting the retaining end of the rod into the end hole;
disposing the intersomatic cage in the disc space in an arcing movement;
releasing the intersomatic cage from the instrument by removing the retaining end of the rod from the end hole;
removing the instrument from the disc space; and
suturing the annulus and the skin.

23. A method according to claim 22, wherein the step of disposing the intersomatic cage in the disc space is preceded or accompanied by a step of articulating a mobile portion of the instrument to a selected angle, said step of articulating the mobile portion being followed by a step of locking the mobile portion at the selected angle.

24. A method according to claim 22, wherein the step of disposing the intersomatic cage in the disc space is followed by the steps of determining the position and orientation of the intersomatic cage in the disc space by detecting a radio-opaque marker comprised in the body of the intersomatic cage with x-rays and, if such position or orientation is improper, adjusting the position or orientation of the intersomatic cage in the disc space.

25. A method according to claim 22, wherein the steps of inserting the end portion of the spatula into the return hole of the intersomatic cage and disposing the arc defined by the body proximal to the arc defined by the spatula are followed by, and the step of fixing the intersomatic cage onto the instrument by inserting the retaining end of the rod into the end hole is preceded by, a step of engaging a pin of the instrument with a recess disposed on the end wall of the intersomatic cage.

26. A method according to claim 22, wherein the step of disposing the intersomatic cage in the disc space is preceded by a step of distraction of the adjacent vertebrae.

* * * * *